United States Patent
Beecher et al.

(10) Patent No.: US 12,354,859 B2
(45) Date of Patent: Jul. 8, 2025

(54) IROA METABOLOMICS WORKFLOW FOR IMPROVED ACCURACY, IDENTIFICATION AND QUANTITATION

(71) Applicant: IROA Technologies, LLC, Bloomfield Hills, MI (US)

(72) Inventors: Christopher Beecher, Chapel Hill, NC (US); Richard A. Yost, Gainesville, FL (US); Robin Hendrikus Johannes Kemperman, Gainesville, FL (US)

(73) Assignee: IROA Technologies, LLC, Chapel Hill, NC (US)

( * ) Notice: Subject to any disclaimer, the term of this patent is extended or adjusted under 35 U.S.C. 154(b) by 0 days.

(21) Appl. No.: 19/014,907

(22) Filed: Jan. 9, 2025

(65) Prior Publication Data
US 2025/0149320 A1    May 8, 2025

Related U.S. Application Data

(60) Continuation of application No. 17/321,009, filed on May 14, 2021, now Pat. No. 12,230,488, which is a division of application No. 15/905,452, filed on Feb. 26, 2018, now abandoned.

(60) Provisional application No. 62/463,153, filed on Feb. 24, 2017.

(51) Int. Cl.
G01N 33/483    (2006.01)
G01N 33/68     (2006.01)
H01J 49/00     (2006.01)

(52) U.S. Cl.
CPC ...... H01J 49/0036 (2013.01); G01N 33/6845 (2013.01); H01J 49/0009 (2013.01); *G01N 2458/15* (2013.01); *G01N 2496/80* (2013.01); *G01N 2560/00* (2013.01)

(58) Field of Classification Search
None
See application file for complete search history.

(56) References Cited

U.S. PATENT DOCUMENTS

| | | |
|---|---|---|
| 7,820,963 B2 | 10/2010 | Beecher et al. |
| 2005/0014279 A1 | 1/2005 | Nguyen et al. |
| 2005/0070022 A1 | 3/2005 | Nguyen et al. |
| 2006/0284068 A1 | 12/2006 | Amirav et al. |
| 2007/0158542 A1 | 7/2007 | Bauer et al. |
| 2007/0176088 A1 | 8/2007 | Li et al. |
| 2008/0146797 A1 | 6/2008 | Heinelt et al. |
| 2008/0305479 A1 | 12/2008 | Van Den Boom et al. |
| 2009/0039246 A1 | 2/2009 | Beecher et al. |
| 2011/0084204 A1 | 4/2011 | Beecher et al. |

FOREIGN PATENT DOCUMENTS

| | | |
|---|---|---|
| EP | 1695088 A1 | 8/2006 |
| WO | WO 2008/042634 A2 | 4/2008 |
| WO | WO 2009/046204 A1 | 4/2009 |

OTHER PUBLICATIONS

U.S. Appl. No. 17/321,009 2022/0037139, filed May 14, 2021 Feb. 3, 2022, Christopher Beecher, IROA Metabolomics Workflow for Improved Accuracy, Identification and Quantitation.
Jan. 9, 2025, Christopher Beecher, IROA Metabolomics Workflow for Improved Accuracy, Identification and Quantitation.
Beecher and de Jong Poster presented at 67th American Society for Mass Spectrometry (ASMS) Conference on Mass Spectrometry and Allied topics, Jun. 2-6, 2019, in Atlanta, Georgia.
Bueschl et al., "Isotopic labeling-assisted metabolomics using LC-MS", Analytical and Bioanalytical Chemistry, Sep. 26, 2012, 405(1): 27-33.
C.W.W. Beecher Curriculum Vitae (CV).
Charkoftaki et al., "An AI-powered patient triage platform for future viral outbreaks using COVID-19 as a disease model", Human Genomics, Aug. 29, 2023, 17: 80.
De Jong, et al., "Addressing The Current Bottlenecks of Metabolomics: Isotopic Ratio Outlier Analysis™, An Isotopic-Labeling Technique For Accurate Biochemical Profiling", Bioanalysis, 2012, 4(18): 2303-2314.
Dwivedi et al., "Metabolic profiling of human blood by high-resolution ion mobility mass spectrometry (IM-MS)", Int. Jounal Mass Spectrom., Dec. 2010, 298(1-3): 78-90.
Enlarged vertically divided center portion of F1a.
Enlarged vertically divided left-hand portion of F1a.
Enlarged vertically divided right-hand portion of F1a.

(Continued)

*Primary Examiner* — Paul S Hyun
(74) *Attorney, Agent, or Firm* — Lathrop GPM LLP; Laura A. Labeots

(57) ABSTRACT

An IROA Matrix of metabolite compounds is disclosed. Each of whose compounds has a molecular weight of 2000 AMU or less, and is present as first and second isotopomers that are equally present at two predetermined isotopomeric balances, and contain 2 to 10% of a first isotope, and 90 to 98% of a second isotope, respectively. A reagent pair for transforming a natural abundance mass spectral analysis metabolite sample into an IROA sample is also disclosed and comprises two reactively identical reagents that constitute first and second isotopomers containing 2 to 10% of a first isotope, and 90 to 98% of a second isotope, respectively. Each of the reagent pair contains the same reactive group that reacts with and bonds to a functional group of one or more compounds present in a composition of biologically-produced metabolite compounds. Methods of making and using the above and related materials are also disclosed.

6 Claims, 36 Drawing Sheets

(56) References Cited

OTHER PUBLICATIONS

Fadil et al., "Correction: Isotope Ratio Outlier Analysis (IROA) for HPLC-TOFMS-Based Metabolomics of Human Urine. Metabolites 2022, 12, 741", Metbolites (2024) 14(6): 293.

Fadil et al., "Isotope Ratio Outlier Analysis (IROA) for HPLC-TOFMS-Based Metabolomics of Human Urine", Metbolites (2022) 12(8): 741.

Freund et al., "Recent advances in stable isotope-enabled mass spectrometry-based plant metabolomics", Current Opinion In Biotechnology 43(7): 41-48 (Sep. 7, 2016).

International Search Report and Written Opinion for PCT International Patent Application No. PCT/US2018/019743, dated Jun. 7, 2018.

IROA Technologies LLC, "TruQuant Yeast Extract Semi-targeted QC Workflow Kit", Chapel Hill, NC (Feb. 28, 2023).

IROA Technologies, 2022, "The perils of a vanity press in scientific publishing", Obtained from the IROA website: <https://subtext.iroatech.com/the-perils-of-a-vanity-press-in-science>.

IROA/SWATH, Product Literature, Sciex, Document No. RUO-MKT-105814-A (2017).

Kemperman et al., Metabolomics; Abstract, MASCL 2018 US, Palm Springs, CA, Jan. 21-25, 2018.

Lippa et al., "Reference materials for MS-based untargeted metabolomics and lipidomics: a review by the metabolomics quality assurance and quality control consortium (mQACC)", Metabolomics, Apr. 9, 2022, 18(4): 24.

Mahmud et al., "An IROA Workflow for correction and normalization of ion suppression in mass spectrometry-based metabolomic profiling data." Res Sq, Feb. 1, 2024.

Metabolomics Methods and Protocols, S.K. Bhattacharya ed., Springer Nature (2019).

Metabolomics Methods and Protocols, S.K. Bhattacharya ed., Springer Nature (2019); Methods in Molecular Biology 1996; volume.

Methods in Molecular Biology 1996, Product literature.

P.R. China; Application No. 201880013676.0, First Action; including English Translation.

P.R. China; Application No. 201880013676.0, Search Report, Including English Translation.

Petrova et al., "Metabolomics of Mouse Embryonic CSF Following Maternal Immune Activation", poster Dec. 24, 2023.

Piqueras et al., "Morphogenesis in Micropropagation", Methods in Molecular Biology 1996, Chapter 15, pp. 443-462.

Poster presented at 2021 American Society of Mass Spectroscopy Annual meeting, Pennsylvania Convention Center in Philadelphia, PA, Oct. 31-Nov. 4, 2021.

Product Literature, Sciex, Document No. RUO-MKT-02-0747-A (2017).

Qiu et al., "Isotopic Ratio Outlier Analysis (IROA) of the S. cerevisiae metabolome using accurate mass GC-TOF/MS: A new method for discovery", Anal Chem., Feb. 17, 2016, 88(5): 2747-2754.

Stupp et al., "Isotopic ratio outlier analysis global metabolomics of Caenorhabditis elegans", Anal. Chem., Dec. 17, 2013, 85(24): 11858-11865.

Supplementary European Search Report for European Patent Application No. 18757142.7, dated Oct. 7, 2020.

Weindl et al., "Isotopologue ratio normalization for non-targeted metabolomics", Journal of Chromatography A, Apr. 10, 2015, 1389: 112-119, Epublished Feb. 17, 2015.

Wu et al., "Quantitative analysis of the microbial metabolome by isotope dilution mass spectrometry using uniformly 13C-labeled cell extracts as internal standards", Analytical Biochemistry, Jan. 15, 2005, 336(2): 164-171.

- IROA for metabolomics studies
  - Identification of all biochemical compounds
  - Sample variance correction
  - Compare experimental and control
  - Determine number of carbons
  - Differentiates noise
- Influence of isomers and isobars
  - Endogenous compounds
  - Exogenous compounds

HPLC 1200 Series
Column: ACE Excel C18-PFP (75 x 3.0 mm, 2 μm)
Mobile phase A: Water + 0.1% formic acid
Mobile phase B: Acetonitrile + 0.1% formic acid Retention time: 7.8 min
Mass Range: 188 – 199 m/z
Drift time: 17.1 ms

- IROA Pattern is easy to recognize biological related compounds
- Number of carbons
- Specific drift time Retention time: 6.3 min
Mass Range: 136 – 141 m/z
Drift times:   15.1 ms
               19.9 ms

* Detection of two IROA patterns in the mobility dimension
* Both endogenous compounds
* Could potentially be:
    * Conformers
    * Isomers
    * Isobars

- Differentiation of overlapping IROA patterns from different compounds
- Recognition of carbon numbers

Fig. 12C

Bin parameters  Bin identification results  Bin component peaks  Individual peak details  MSMS details
MSMS plot  MSMS table  MSMS analysis
MSMS patterns  MSMS mass differences

| Name | M/Z C12 | M/Z C13 | Number of carb... | Formula | Loss | Area | Is parent |
|---|---|---|---|---|---|---|---|
| 166.0870 ~ 175.1162 | 166.087 | 175.116 | 9 | C9H11NO2 | | 44,855 | ✓ |
| 131.0479 ~ 140.0795 | 131.048 | 140.079 | 9 | C9H7O | H4N | 38,599 | ☐ |
| 120.0810 ~ 128.1064 | 120.081 | 128.106 | 8 | C8H10N | CHO2 | 2,504,012 | ☐ |
| 107.0483 ~ 114.0719 | 107.048 | 114.072 | 7 | C7H7O | C2H4N | 36,798 | ☐ |
| 103.0555 ~ 111.0816 | 103.055 | 111.082 | 8 | C8H7 | CH4NO2 | 1,009,814 | ☐ |
| 93.0701 ~ 100.0935 | 93.07 | 100.093 | 7 | C7H9 | C2H2NO2 | 88,261 | ☐ |
| 91.0564 ~ 98.0784 | 91.056 | 98.078 | 7 | C7H7 | C2H4NO2 | 71,683 | ☐ |
| 77.0419 ~ 83.0520 | 77.042 | 83.062 | 6 | C6H5 | C3H6NO2 | 78,229 | ☐ |

IROA METABOLOMICS WORKFLOW FOR IMPROVED ACCURACY, IDENTIFICATION AND QUANTITATION

CROSS-REFERENCE TO RELATED APPLICATIONS

This application is a continuation of U.S. patent application Ser. No. 17/321,009, filed May 14, 2021, which is a division of U.S. patent application Ser. No. 15/905,452, filed Feb. 26, 2018, which claims the benefit of Provisional Patent application No. 62/463,153, entitled "Implementing IMS-assisted IROA for Metabolomics" filed on Feb. 24, 2017, whose disclosures are incorporated by reference.

BACKGROUND ART

Metabolites are small molecular weight compounds (less than about 2000 Da and more usually less than about 1000 Da) that are employed as building blocks or produced as end products in various metabolic pathways and cellular regulatory processes in a biological system. The entire collection of metabolites in a biological system, whether at the cellular, pathway or organism level, is known as a "metabolome". Levels of these metabolites in a metabolome are either dictated by the genome, proteome, and/or transcriptome of the biological system or imposed by environmental perturbations and results in changes in phenotype. Thus, metabolomics can be applied to map or identify the cause of alteration in phenotype and understand correlations between "omics". Dwivedi, et al., *Int J Mass Spectrom* 2010 298: 78-90.

Isotopic Ratio Outlier Analysis (IROA) has been developed to enable the characterization of carbon information in a given metabolites or a fragment. Unlike other stable isotope labeling methods, rather than utilizing substrates with natural abundance (1.1% of 13C isotopomer seen in carbon atoms in nature) and 98-99% enrichment for the control and experimental populations, respectively, IROA with prototrophic yeast uses randomized 95% 12C glucose (5% 13C), and 95% randomized 13C glucose (5% 12C) as carbon sources. This strategy leads to more predictable and diagnostic patterns for the observable isotopic peaks in the mass spectra. [Qiu et al., Metabolites 2018 8:9].

The promise of IROA for metabolic phenotyping has been demonstrated in model organism studies. *Saccharomyces cerevisiae*, a prototrophic wild-type strain in the CEN.PK background [Brauer et al., *Mol. Biol. Cell* 2005, 16:2503-2517] was grown in minimal yeast nitrogen base (YNB) media, containing either randomized 95% 12C, or 95% 13C glucose as the main carbon source, in order that the isotopomer pattern of all metabolites would mirror the labeled glucose [Qiu et al., *Anal. Chem.* 2016, 88:2747-2754], a protocol that can easily be adapted for microbial species studies.

The abundance of the light isotopologues in the 95% 13C samples ($M_{n-1}$, $M_{n-2}$, etc., the 13C envelope) or the heavy isotopologues in the 95% 12C samples ($M_{0+1}$, $M_{0+2}$, etc., the 12C envelope), follows the binomial distribution for 13C, based on the initial substrate enrichment, in the metabolite products generated. The mass difference between the 12C ($M_0$) isotopic peak and the 13C ($M_n$) isotopic peak indicates the number of carbons (n) in the metabolite's carbon backbone. This narrows possibilities for chemical formula generation (CFG) and for normalization between control (13C) and treated (12C) groups. [Qiu et al., *Metabolites* 2018 8:9].

It is possible to use metabolomic techniques, such as the IROA basic, or IROA phenotypic protocols (optimally) [de Jong and Beecher, C. *Bioanalysis* 2012, 4 (18):2303-2314], or standard metabolomic techniques to identify and crudely quantify several hundred or even thousands of compounds in a biological sample. However, to make such measurements and to compare the measurements from any two or more samples, all the samples need to be analyzed in a single batch, ideally during a single day because day-to-day variances are too great to otherwise overcome, and absolute quantitation; i.e., relative to a known standard, cannot be assured.

It is currently not quantitatively acceptable to compare samples run on the same instrumentation several days apart, and impossible to compare data generated on different instruments, or based on different methods. Instrument drift, chromatographic drift, and even environmental conditions can alter results sufficiently so that reproducibility is hard to obtain even on the same instrument. In addition to these problems of quantitation, the identification of any compound across many mass spectral techniques alone is unlikely to be successful unless very careful calibrations have been made and authentic standards are run. This is because, not only are there multiple biological compounds that can be confused because they have the same exact mass but, even more problematic, there are often more artefactual or fragmentary compounds that are structurally different from, but can share the correct mass, or even formulae, as biological isobaric equivalents.

The invention disclosed hereinafter extends methods described in the following U.S. Pat. No. 7,820,963, the basic IROA patent, issued Oct. 26, 2010, referred to hereinafter as IROA963; U.S. Pat. No. 7,820,964, issued Oct. 26, 2010, and referred to hereinafter as IROA964; U.S. Pat. No. 8,168,945, issued May 1, 2012, referred to hereinafter as IROA945; U.S. Pat. No. 8,536,520, issued Sep. 17, 2013, referred to hereinafter as IROA520; and U.S. Pat. No. 8,969,251 that issued Mar. 3, 2015, and is referred to hereinafter as IROA251. These patents and the art cited therein are incorporated herein by reference.

The IROA protocols rely on the creation of isotopic patterns that are mathematically informative to insert information into biological samples to provide better identification and quantitation of the individual chemical components when the samples are subjected to mass spectral analysis. Traditional methods required chromatographically clean; i.e., "baseline", separation to achieve the best quantitative accuracy, the IROA protocols do not and hence can be used in the quantitation of very chemically complex samples where such separation is not consistently possible.

The exemplary samples studied were uniformly and universally labeled with appropriate isotopes. An element in which there are two stable isotopes that are not significantly distinguished by enzymes or living systems is preferably used. Carbon (specifically, 12C and 13C) is used for purposes of illustration herein because of its universal applicability. However, additional examples are well known to a worker of ordinary skill.

The use of isotopes that exhibit minimal biological isotope effect is of import. For instance, the use of the isotopes of hydrogen such as deuterium (D) is not suitable because it frequently causes an observable effect on metabolism due to the fact that the deuterium isotope has a mass that is twice that of hydrogen, and thus causes a reduction in the kinetics of some enzyme mechanisms. Tritium (T) is radioactive and thus not stable to decay.

In many of these protocols the production of the IROA patterns relies on the creation of molecules where the probability of all carbons in a molecule is carefully constrained to a close range of isotopic probabilities. Illustratively, for a system using stable isotopes of carbon [carbon-12 (12C) and carbon-13 (13C)], the isotopic ratios in this example specifically include a dilution of five to ten percent of one carbon isotope in another; i.e., one sample is grown on a carbon source (nutrient in a medium) that can be 95% carbon-12 (12C) and 5% carbon-13 (13C), hereinafter called "C-12 medium", and in such a situation the other sample is grown in mirrored medium that contains a nutrient that contains 95% carbon-13 and 5% carbon-12 in a medium, hereinafter called "C-13 medium". In each of these cases the biological system takes up the nutrient in the medium and grows upon it in such a way as to transform itself so that all of its parts are distinctively identifiable as to their origin. Further information can sometimes be obtained by incorporating a second set of two isotopes of a second atom present at two different predetermined isotopic ratios into the nutrient compositions.

When the two samples are mixed, intermingled or otherwise composited, the composite sample contains molecules from both the "control" (that are made up of a substantial majority, e.g., 90% to 95%, of 12C) and the "experimental" (that are made up of a substantial majority, e.g., 90% to 95%, of 13C). Deviating significantly from the 90% to 95% ratio taught by this method reduces the potential for interpretation as is taught in IROA963, although 98% and 2% of the carbon isotopes have been successfully used.

More specifically still, the probability can be set to 95% C-13 in an illustrative IROA standard sample. In such a standard all the molecules contained in it exhibit the property that the probability for of its carbons will be as close to 95% 13C as is achievable. Such IROA molecules have many special properties, namely:

1) The isotopic balance of 12C to 13C is so much larger than the natural abundance probability of approximately 1.1% and yet is specifically not approaching 100%, therefore each molecule presents itself as a collection of isotopomeric sets of that molecule with the mass of each set differing by the mass of exactly one carbon neutron, or approximately 1.00335 AMU. These sets are significantly larger and more complex than natural abundance equivalents and can be easily identified.
2) The distribution of isotopomers across the above sets is a function of the number of carbons in the molecule and the probability of a 13C in each such position. The presence of isotopomeric sets contributed from other natural abundance sources of hydrogen, oxygen, nitrogen, etc. are so small that their patterns are equally distributed into and insignificant to the C13 isotopomeric sets.
3) The amount of isotopomers for each IROA molecule can be deduced in a mass spectrometer as the height of a peak, and therefore the relative concentration of all isotopomeric sets creates a pattern of peaks for each molecule. This pattern is effectively defined as a binomial distribution the percent (x), and the number of carbons (n), and therefore can be calculated as probabilities, $((1-x)+(x))^n$.
4) These IROA patterns are dominant features of any mass spectral analysis of an IROA sample. Because the patterns themselves can be quite complex, their occurrence due to random peak noise is effectively nonexistent. Software was developed that identifies these patterns with great accuracy.
5) The C12 and C13 monoisotopic masses of such a molecule cannot be seen but can be determined by inspection of the shape of the patterns seen. The monoisotopic mass constrained by the number of carbons effectively is an unique determinant of the molecular formula of the molecule, significantly more accurate than attempting to solve the polynomial equations required for natural abundance molecules.
6) Aside from the mass differences of their isotopomeric sets, the molecules are otherwise indistinguishable and thus perform very similarly through almost all treatments and generally have the same physical characteristics. This characteristic of IROA peaks is a basis of the IROA Identification Techniques.

There are many IROA protocols based on these properties. The following two IROA protocols are relevant to this invention.

The Basic IROA Protocol

The basic IROA protocol (which was described in IROA963, and continued in IROA945, and IROA520) creates two populations of IROA molecules containing widely different amounts, typically 90-95% and 10-5% of the first and second isotopes, respectively, and 10-5% of the first isotope with 90-95% of the second isotope. Isotopes other than hydrogen and deuterium are preferred such as the particularly preferred approximately 5% C13 and approximately 95% C12 used with approximately 5% C12 and approximately 95% C13.

In both populations, the distribution of C13 in every compound is random and universal and the probability of a carbon being either a C12 or a C13 is the stated value, here either approximately 5% or 95%. The experimental "base" population of molecules (C12-B) with approximately 5% C13 and the remaining carbons (95%) are C12. The control "Internal Standard" population (C13-IS) sample made up of approximately 95% C13 and 5% C12.

Because both the C12-B and C13-IS are made up of IROA molecules:

1) For any given molecule their respective peak patterns are different, but both solve to the same molecular formula. The C12-B monoisotopic peak has a distinct M+1, M+2 peaks, and possibly additional M+n peaks. The C13-IS monoisotopic peak has a distinct M−1, M−2 peaks, and likely additional M-n peaks.
2) Unlike isotopomers based on deuterium, these isotopomers co-chromatograph and exhibit very similar physical properties except for mass.
3) IROA compound peaks can only be created in most experimental systems through biological means (IROA520), but intentional synthetic IROA compounds (IROA964) can also be prepared and added. In this workflow, the presence of an IROA signal assures that all IROA patterns can come only from the C13-IS or the C12-B, and that they are immediately distinguishable from artefact, electronic noise, or any spurious signals that are always be based on natural abundance isotopic signatures.
4) When the patterns from the same molecule from both the C12-B sample and the C13-IS are found in the same sample, the paired signal is a triply redundant information system in which:
    a) the number of carbons in the molecule can be determined by the ratio of the height of the M+1 to the C12-B monoisotopic for the IROA molecules coming from the experimental samples, b) the number of carbons in the molecule can be determined by the ratio of the height of the M−1 to the C13-IS monoisotopic peak for the IROA molecules coming from the C13-IS samples, and c) the number of carbons in the molecule can be determined by the mass difference between the monoisotopic mass of the molecules coming from the experimental sample, and the mass of the monoisotopic from the C13-IS.

When all three of these calculations indicate the same number of carbons, it is extremely likely that the pattern has been correctly found, and that the probability of error is extremely low. Because discovery of these patterns can be entirely software-driven, the discovery of such peaks is a completely automatable task (IROA945).

The basic IROA protocol permits for a completely unbiased (or non-targeted) analysis of an experimental sample in which the C12-B can be made to vary according to an experimental design for purposes of discovery of the biological effect of such experimental design. In such a sample the C12-B population is derived from an experimental sample, and if a molecule does not happen to be in either the C13-IS or the C12-B sample, the presence and probable identification of the molecule is still possible, and the absence of the molecule in the other is an establishable fact.

Although not triply redundant, the presence of a randomly created (i.e. artefactual) IROA peak is so low that a single IROA peak is easily identified as such and can be quantified. This basic IROA protocol is therefore suited to experimental situations in which the ability to find and characterize all the peaks of biological origin in either the C12-Bl or C13-IS, thereby identifying those situations in which a molecule is present in one but missing from the other.

The triple redundancy of the basic IROA protocol is such a strong algorithm that it is possible to find very weak signals even in the presence of very strong noise by simply enforcing the peak shape requirements.

In the case of Matrix, where the C12-B and C13-IS sides are both of equal chemical composition and matching isotopic balance, by design, the requirement for symmetry makes it easy to find many very small peaks in deep noise situations with little chance of error. Thus, Matrix represents a special case of the IROA Basic protocol in which its characteristics are so predictable as to make the information derived from it especially reproducible and capable of being found at extremely low levels of detection.

The IROA Workflow is based on this unique property. The source of material for Matrix can be either biological or synthetic. The IROA Identification Techniques can be applied to any IROA peak to further strengthen the identification of the underlying compound.

The Phenotypic IROA Protocol

The Phenotypic IROA protocol is a protocol for situations in which it is not feasible or practical to label the experimental sample itself but a common and consistent 95% (+/−3%) IROA internal standard, such as the above described C13-IS, is used to assure accurate identification of a molecule and accurate quantitation. The Phenotypic Protocol is useful for the analysis of human (clinical) samples, agricultural samples, industrial samples, or other situations where the size or the source of the experimental samples is such that it is simply not feasible to label them. However, the Phenotypic protocol, by providing a common rigorous IROA internal standard, provides a more accurate route for the identification and quantification of a large number of compounds that are found in the sample natural abundance isolates.

Unlike the "unbiased" or "non-targeted" analysis of basic IROA, Phenotypic IROA is a targeted quantitative analysis of a very large number of compounds based on a very chemically complex IROA internal standard (IS). A C13-IS can contain well over 1000 compounds (potentially unlimited), but the IROA properties outlined earlier do not require complete chromatographic separation to assure both the identity and quantitation of all the compounds contained in the IS.

The Phenotypic protocol puts an IROA internal standard into every natural abundance sample and uses the dual pieces of information from the C13-IS, 13C-monoisotopic mass and number of carbons, to locate the natural-abundance isotopomer of the same compound. Correlation of the natural abundance time-resolved chromatographic profile of the found peak, and it's natural-abundance isotopic form are then used to support the IROA-based identification.

Because the IROA peaks are informatically self-contained, it is possible to correctly identify and quantify multiple co-eluting peaks. In the case of the Phenotypic Protocol, the IS can be created by a worker to provide support for the unique quantitation needs of the experimental system. Thus, a wheat researcher, can create a wheat C13-IS that can be used because it contains a chemical profile more reflective of wheat biochemistry, but this C13-IS is used primarily to find and identify IROA peaks in wheat and quantify their natural abundance counterparts. Although the triple redundancy of the Basic IROA protocol does not exist in the Phenotypic protocol, the signal is still redundant in that the 95% C13-IS provides a mass and number of carbons to determine exactly where the natural abundance monoisotopic signal is found (see FIG. 10F).

In the IROA workflow, the same C13-IS is used in both the Matrix and the Clinical or experimental samples and the chemical information derived from the Matrix sample is used to verify and validate the compounds found in the clinical or experimental (Phenotypic) samples. The Phenotypic samples can be analyzed for chemical information to the same extent as the Matrix samples but this is not required. For instance, whereas the Matrix samples need to be analyzed to completely characterize every compound present in it, it can be sufficient to use the mass and retention information derived from the analysis of the Matrix to find the same compounds in the experimental or clinical samples, and use a higher acquisition rate than would be possible in the Matrix samples to achieve a higher quantitative accuracy.

BRIEF SUMMARY OF THE INVENTION

In one aspect, the present invention contemplates an IROA Matrix composition of biologically-produced metabolite compounds. Each of those metabolite compounds has a molecular weight of about 2000 AMU or less. Each of the metabolite compounds is present as first and second isotopomers that are equally present at two predetermined isotopomeric balances. The first isotopomers contain about 2 to about 10% of a first isotope, and the second isotopomers contain about 90 to about 98% of a second isotope of the same atom. The first and second isotopes are stable to radioactive decay and are other than hydrogen and deuterium.

The biologically-produced metabolite compounds are obtained from a cell lysate preparation obtained from culture of single-celled or multi-celled organisms, and the molecules are randomly and universally labeled with isotope pairs of one or more elements selected from the group consisting of isotopes of carbon (12C and 13C), nitrogen (14N and 15N), oxygen (16O, 17O, or 18O), sulfur (32S, 33S, 34S, or 36S), chlorine (35Cl and 37Cl), magnesium (24Mg, 25Mg and 26Mg), silicon (27Si, 28Si and 29Si), calcium (40Ca, 42Ca, 43Ca, and 44Ca), and bromine (79Br and 81Br).

Another contemplated aspect of the invention is a method of creating a reference library of identity data of compounds in an IROA Matrix as described above, and comprises the steps of 1) mass spectrally determining the identity of the compounds of an IROA Matrix that are within the resolution and sensitivity of the apparatus to provide its symmetrical IROA peak pattern, and additionally determining one or more of: a) the gas and/or liquid chromatographic properties of the compounds present, b) the collisional cross section of the compounds present, and c) the fragmentation pattern of the compounds present. The compound identity data so determined is maintained for use in identifying one or more of the same compounds in a later-analyzed sample. The reference library of identity data of compounds in an IROA Matrix is itself also contemplated. The use of one or both of compound collisional cross sections and fragmentation patterns are preferred in conjunction with mass spectral identification.

A further contemplated invention is a method of quantifying and identifying compounds in a natural abundance sample using an Internal Standard that is of the same chemical composition as isotopomers containing the about 90 to about 98% of the heavier molecular weight isotope-containing compounds of an IROA Matrix composition and is inserted into that natural abundance sample. Each compound in the Internal Standard is itself identified in a before-described reference library of identity data. It is preferred that the quantity of each identifiable compound of the natural abundance sample is determined, and more preferably, the quantity of each natural abundance sample compound is determined relative to the Internal Standard.

Yet another aspect of the invention is a method of measuring quality assurance and/or a quality control on the operational constancy of a mass spectral apparatus and associated ion mobility channel and chromatographic apparatus, when present. That method comprises the steps of assaying the sample of an IROA Matrix composition as described above, and determining whether the same sets and amplitudes of symmetric IROA mass spectral peaks are present in each analysis. The preferences noted above in regard to an IROA Matrix composition are repeated here and in each time a Matrix composition or its components are used herein.

A still further aspect of the present invention contemplates a reagent pair capable of transforming a natural abundance mass spectral analysis metabolite sample into an IROA sample. That reagent pair comprises two reactively identical reagents that constitute first and second isotopomers. The first isotopomers contain about 2 to about 10% of a first isotope, and the second isotopomers contain about 90 to about 98% of a second isotope of the same atom. The first and second isotopes are stable to radioactive decay and are other than hydrogen and deuterium. Each of the reagent pair contains the same reactive group that reacts with and bonds to a functional group of one or more compounds present in a composition of biologically-produced metabolite compounds. Each of the biologically-produced metabolite compounds of the natural abundance mass spectral analysis sample has a molecular weight of about 2000 AMU or less.

A reagent pair reactive group reacts with and bonds to a biologically-produced metabolite functional group selected from the group consisting of one or more of an amine, aldehyde or ketone, hydroxyl, thiol and carboxylic acid. Preferably, a reactive group reacts with and bonds to an amine functional group. A preferred reactive group is a isothiocyanate reactive group, and the reagent pair are isotopomers of phenylisothiocyanate whose first isotopomers contain about 2 to about 10% of a first isotope, and whose second isotopomers contain about 90 to about 98% of a second isotope. An alternative pair of reagents are IROA isotopomers of a hydrazine or a semicarbazide that react and bind to carbonyl groups of aldehyde and ketone groups present in a natural abundance mass spectral analysis metabolite sample.

BRIEF DESCRIPTION OF THE DRAWINGS

In the drawings forming a portion of this disclosure,

FIG. 10A is a mass spectrum of arginine in which C12 and C13 are present in natural abundance, whereas

FIG. 12C provides IROA diagnostic structural information via fragment interpretations from the peaks of FIG. 12B;

DEFINITIONS

Figure 1A:
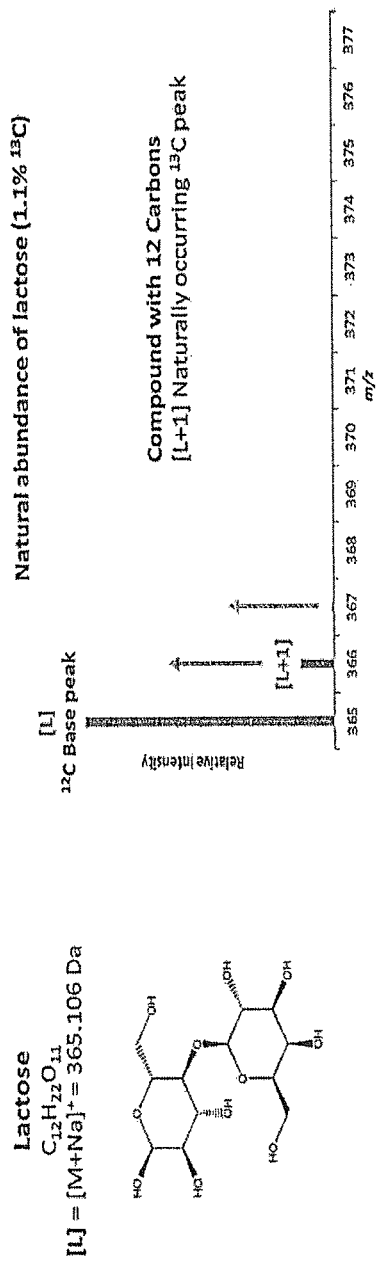
FIG. 1A shows the mass spectral peaks obtained on the analysis of lactose that contains naturally abundant amounts of 12C and 13C.
Figure 1B:
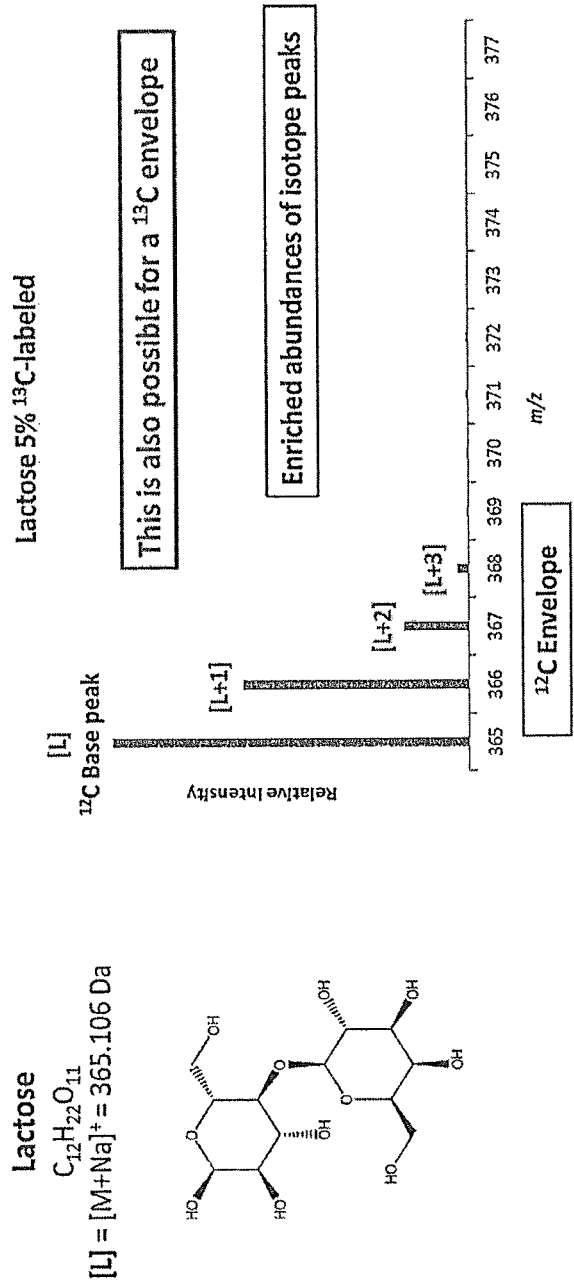
FIG. 1B shows the mass spectral peaks obtained on the analysis of lactose that contains 95% 12C and 5% 13C.
Figure 1C:
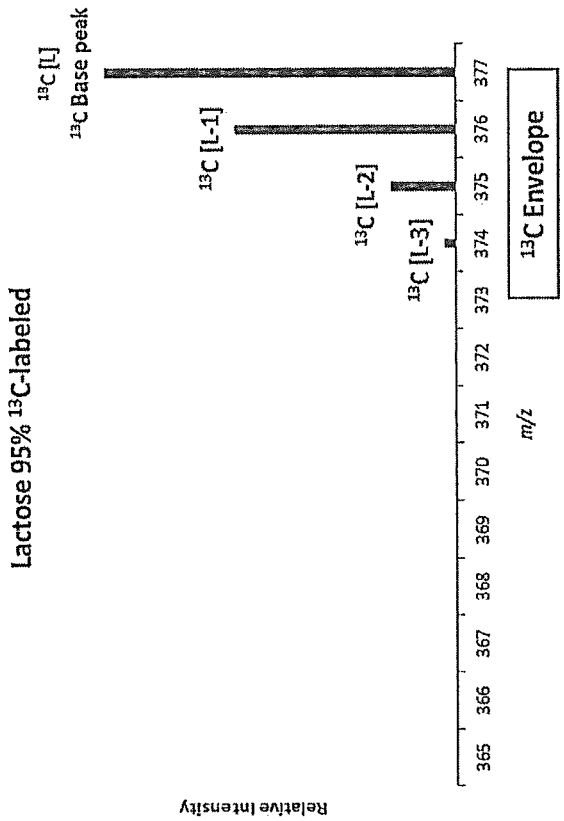
FIG. 1C shows the mass spectral peaks obtained on the analysis of lactose that contains 5% 12C and 95% 13C.
Figure 1C:
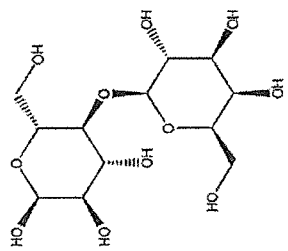
Figure 1D:
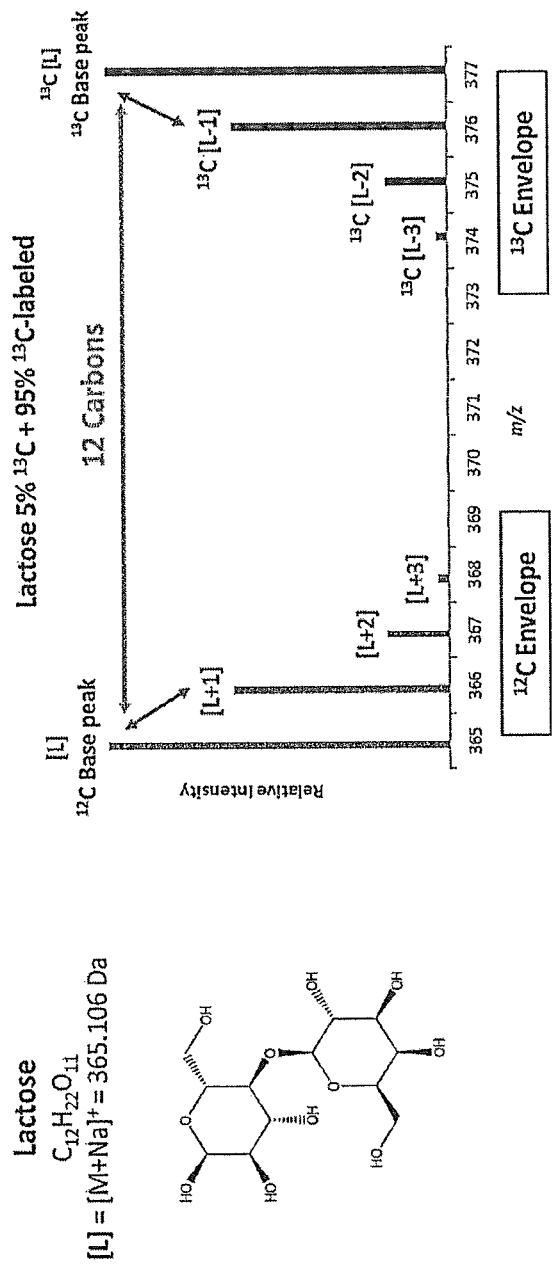
FIG. 1D shows the mass spectral peaks obtained on the analysis of lactose that contains equal amounts of lactose that contains 5% 13C with 95% 12C along with 95% 13C and 5% 12C.
Figure 2:
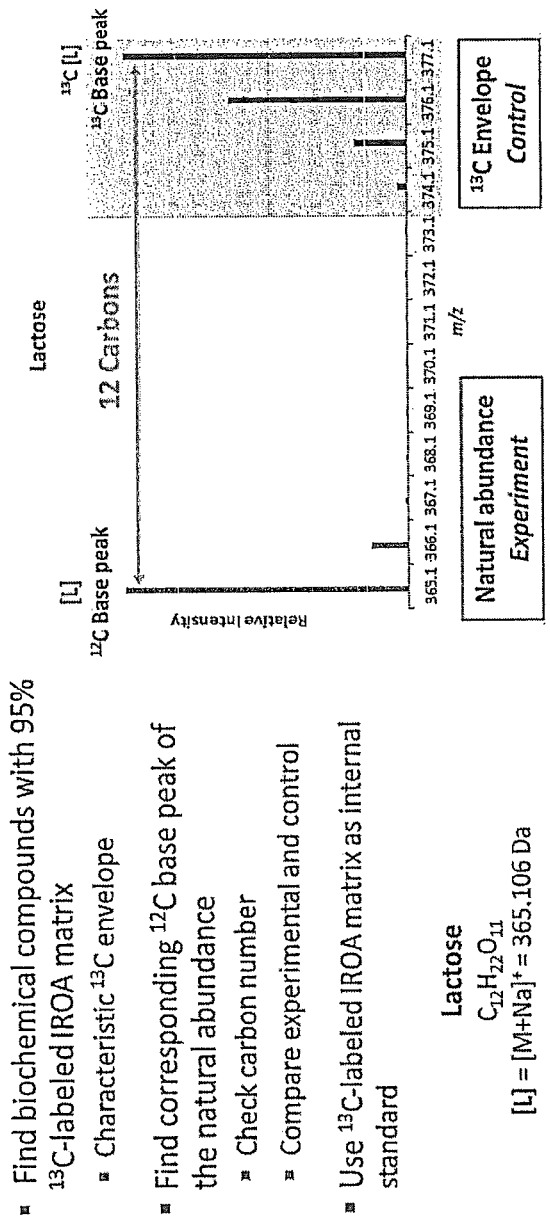
FIG. 2 illustrates the spectra of lactose containing natural abundance of both 12C and 13C as well as peaks obtained from lactose containing 95% 13C, and illustrates the number of carbon atoms in the assayed molecule by the difference in m/z value of the two base peaks being 12 AMU.
Figure 3:
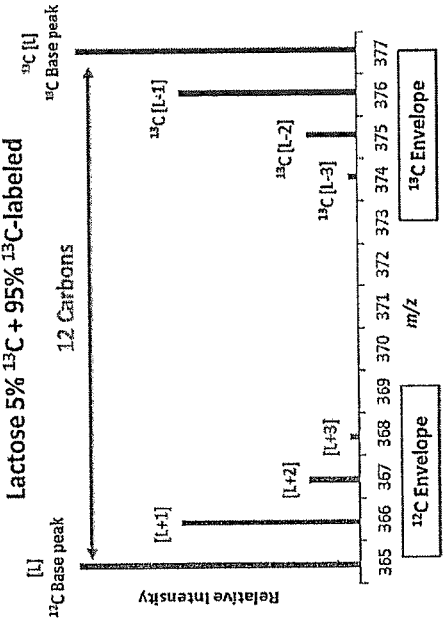
FIG. 3 illustrates the symmetrical arrangement of IROA peaks with the difference between the m/z values for the two base peaks defining the number of carbon atoms present in the assayed compound. See, e.g., de Jong, F. A.; Beecher, C. *Bioanalysis* 2012, 4 (18), 2303-2314.
Figure 4:
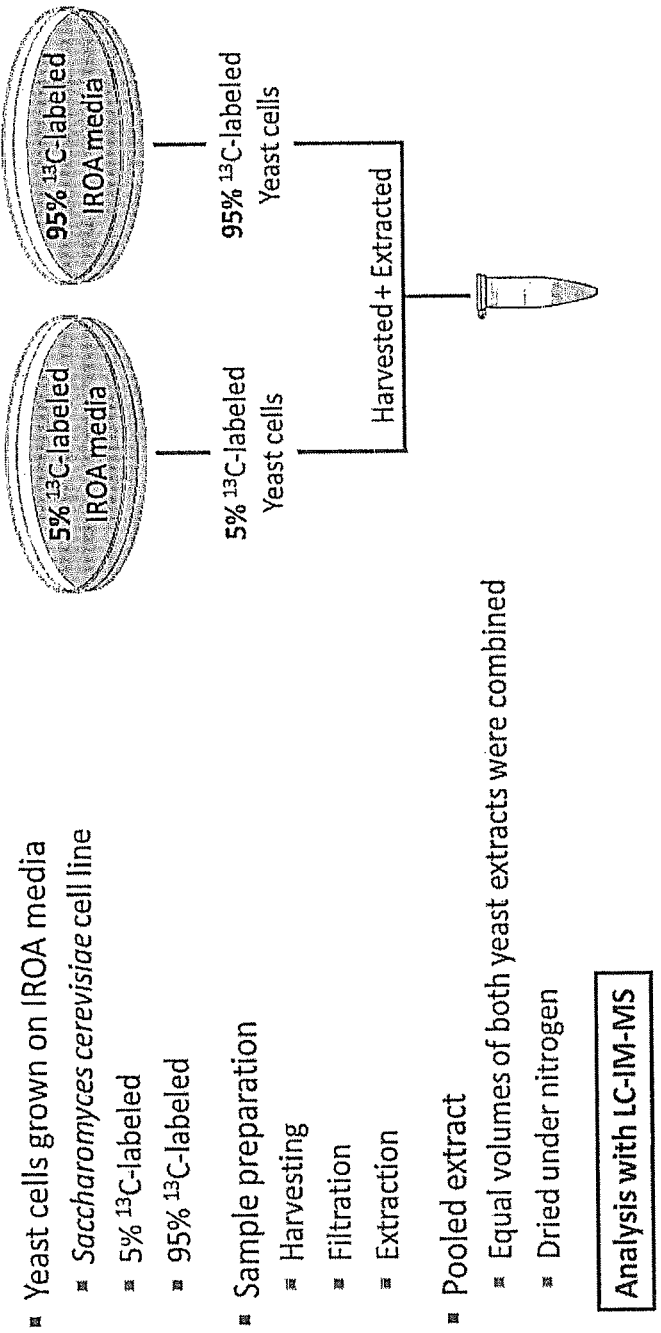
FIG. 4 broadly illustrates steps in the preparation of an IROA sample prepared separately from *Saccharomyces cerevisiae* grown in a medium that contains 5% 13C or 95% 13C as the main source from which a solvent-soluble (usually water) cell lysate is prepared, providing two solutions that contain the same amount of each yeast metabolite compound present and containing either 5% 13C or 95% 13C, which are then combined to form a pooled extract that is freeze-dried to form a reconstitutable IROA standard referred to herein as "Matrix". See, e.g., Qiu, et al., *J. Anal. Chem.* 2016, 88 (5), 2747-2754.

As used herein, the abbreviations "13C", "C13" and "$^{13}C$" all refer to the isotope of the element carbon that has an atomic weight of 13 AMU. Similarly, the abbreviations "12C", "C12" and "$^{12}C$" all refer to the isotope of the element carbon that has an atomic weight of 12 AMU.

Chromatography can mean any form of a chemical separation, including but not limited to all forms of liquid chromatography (LC), gas chromatography (GC), capillary electrophoresis (CE), ion mobility (IM), solid phase extraction (SPE), etc.

Compound identification means any method of determining the physical characteristics of a chemical compound, including but not limited to mass spectroscopy (ms), fragmentation (msms), charge and electronic properties (ms, IM, etc.), shape (IM, drift, etc.), bond and vibrational properties (various spectroscopic methods), and it's IROA form (base mass and number of carbons).

A Matrix is a standard well-defined Basic IROA mixture of compounds such as metabolites, including anabolite and catabolite molecules, or other compounds utilized or present in a given study and contains at least one compound a pair of stable isotopes of the same element that differ in molecular weight (AMU) by at least one AMU. The two isotopes are present in the molecules of that at least one compound in a predetermined ratio that is other than the naturally occurring ratio of those isotopes.

Various Matrices exist, but each matrix supports a specific analytical system, such as plasma, human biopsies, wheat, urine, etc. In addition, a plurality of Matrices can be prepared for the same specific analytical system.

A library is a group of compounds known to be present in a Matrix.

An Internal Standard (IS) is a chemical mixture of compounds that can represent either the lighter or heavier set of IROA compounds such as metabolites, subset thereof of a Matrix sample, or other compounds present or utilized in a Matrix sample of a given study, and is inserted exogenously into every sample that is to be analyzed. Like a Matrix, the IS is a standard well-defined mixture of compounds. The chemical compositions of both the Matrix and IS are ideally identical.

As used herein, predetermined first and second stable isotope amounts are preferably present in "inverted ratios" of each other such as those discussed immediately above in which the number of the numerator of the first ratio is the number of the denominator of the second ratio, and the number of the denominator of the first ratio is the number of the numerator of the second ratio.

Taking the above ratios of 95% and 5%, a first ratio would be 95/5 12C/13C in the C-12 medium, whereas the second, inverted ratio, would be 5/95 12C/13C in the C-13 medium. It is to be understood that a contemplated set of ratios need not be 95/5 and 5/95, and although those amounts are particularly preferred, they are used herein for convenience.

It is to be understood that the first and second stable isotopes present in a Matrix or any other exogenously provided composition such as an internal standard are predetermined and as are their respective amounts of each isotope. As a consequence, the words "predetermined" and "stable" are rarely used herein with their presence implied to minimize verbosity.

DETAILED DESCRIPTION OF PREFERRED EMBODIMENTS

A first aspect of this invention contemplates an IROA Matrix composition of biologically-produced metabolites, including anabolite and catabolite molecules, that is typically a room temperature solid that is dispersible or soluble in an aqueous medium (as defined hereinafter). The individual metabolites have a molecular weight of less than about 2000 AMU, preferably about 1500 AMU or less, and more preferably less than about 1000 AMU. The lower weight limit for a contemplated metabolite is about 60-75 AMU as in acetic acid and glycine.

Every compound is equally present at both of two predetermined isotopomeric balances such that each of the isotopomers is present at about 2 to about 10% of isotope one and at about 90 to about 98% of isotope two. Illustrative useful first and second isotopes of the same atom are one or more elements that include the isotopes of carbon (12C and 13C), nitrogen (14N and 15N), oxygen (16O, 17O, or 18O), sulfur (32S, 33S, 34S, or 36S), chlorine (35Cl and 37Cl), magnesium (24Mg, 25Mg and 26Mg), silicon (27Si, 28Si and 29Si), calcium (40Ca, 42Ca, 43Ca, and 44Ca), and bromine (79Br and 81Br). The first and second isotopes are stable to radioactive decay (can be used in a laboratory without added protection from possible radiation injury), and are other than hydrogen and deuterium.

Put more explicitly in terms of the particularly preferred isotopes, C12 and C13, one group of isotopomers contains about 2 to about 10% C13 and the other group contains about 90 to about 98% C13. Preferably, a first group contains about 5 to about 10% C13 and the second group contains about 90 to about 95% C13, with the remaining carbon atoms being C12 in each instance. It is particularly preferred that the first group contains about 5% C13 and the second group contains about 95% C13, with the remaining carbon atoms being C12. This means that the IROA peak shape for each compound ideally is comprised as a perfectly balanced, symmetrical collection of peaks, with each half a mirror image of the other.

It is to be understood that the above-stated percentages are intended to be identifiably different from the natural abundance amounts of the two isotopes used. Thus, in the case of carbon isotopes, whose natural abundances are 98.89% for C12 and 1.11% for C13, use of about 90 to about 98% for one isotope and about 2 to about 10% of the other isotope permits the analytical equipment to readily distinguish between natural abundance peaks and those provided by an IROA Matrix. Use of the term "about" for the percentage of one or the other isotopomers present is meant to be within ±3% of the stated amount. Thus, the above isotope percentages are known and predetermined, but use of specific amounts within the ranges stated is mostly a matter of convenience.

It is also to be understood that trace, impurity amounts of the element used for an IROA study, here carbon, can also be present among the atoms of that element. Such trace amounts are typically of no consequence to a study. For example, the *Handbook of Chemistry and Physics*, 54$^{th}$ ed., CRC Press, Cleveland, OH, page B251, 1973-1974, lists the natural abundance of C12 and C13 as being 98.89 and 1.11 percents, respectively, with the presence of C14 being reported, but not its percent amount.

It is still further to be understood that use of the words "first" and "second" in regard to the isotopes and the several compositions that can contain them is only for purposes of clarity to distinguish the isotopes, and is not meant to imply anything concerning the order of carrying out any manipulations.

It is preferred that IROA matrices be prepared in relatively large quantities, such as about 10 to about 100 g for an industrial scale and about 10 to about 1000 mg on a laboratory scale so that each batch can be utilized over many spectral analyses. The obtained Matrix composition is preferably kept frozen such as at −80° C. until used to maximize its chemical stability and analytical reproducibility.

Another contemplated aspect of the invention is a method of creating a reference library of identity data of compounds in an IROA Matrix as described above, and comprises the steps of 1) mass spectrally determining the identity of the compounds of an IROA Matrix that are within the resolution and sensitivity of the apparatus to provide its symmetrical IROA peak pattern, and additionally determining one or more of: a) the gas and/or liquid chromatographic properties of the compounds present, b) the collisional cross section of the compounds present, and c) the fragmentation pattern of the compounds present. The compound identity data so determined is maintained for use in identifying one or more of the same compounds in a later-analyzed sample. The reference library of identity data of compounds in an IROA Matrix is itself also contemplated. The use of one or both of compound collisional cross sections and fragmentation patterns are preferred in conjunction with mass spectral identification.

A further contemplated invention is a method of quantifying and identifying compounds in a natural abundance sample using an Internal Standard that is of the same chemical composition as isotopomers containing the about 90 to about 98% of the heavier molecular weight isotope-containing compounds of an IROA Matrix composition and is inserted into that natural abundance sample. Each compound in the Internal Standard is itself identified in a before-described reference library of identity data. It is preferred that the quantity of each identifiable compound of the natural abundance sample is determined, and more preferably, the quantity of each natural abundance sample compound is determined relative to the Internal Standard.

Another aspect of the invention contemplates a method of quality assurance and/or a quality control on the operational constancy of a mass spectral apparatus and associated ion mobility channel and chromatographic apparatus, when present. This method contemplates carrying out a mass spectral analysis on multiple Matrix samples during the course of carrying out analyses of different samples, and determining whether the same sets of symmetric IROA mass spectral peaks are present in each analysis. Illustratively, a Matrix sample can by analyzed before an experimental sample is analyzed, after an experimental sample is analyzed, after the next experimental sample is analyzed. Interpretation of these Matrix analyses is discussed elsewhere herein.

Use of the above technique permits the user to simultaneously validate and quantitate a compound that is present in a complex mixture without the need for a prior baseline separation. This technique benefits from the fact that a collection of isotopomeric ions of any compound, e.g., a C-13 based Isotopic Ratio Outlier Analysis (IROA) peak, an IROA pooled peak, or any other combination of isotopomeric forms of the same molecule, down to and including the dual collection of a C-12 monoisotopic isotopomer paired with the C-13 monoisotopic peak, or even isotopomers based on isotopomers of other elements, such as nitrogen, oxygen, sulfur, or others, share the same collisional cross section (CCS). As a consequence, the isotopomer ions pass through an ion mobility (IM) channel, e.g., high-field asymmetric waveform ion mobility spectrometry (FAIMS), differential mobility spectrometry (DMS), structures for lossless ion manipulation (SLIM), trapped ion mobility spectrometry (TIMS), and other drift tube and/or ion mobility spectrometric (IMS) technologies to emerge at the same time as the same collection that entered when it exits, or in a predictable fashion therefrom.

The entire such collection of ions can then be subjected to a fragmentation, which yields fragment ions, all of which bear the same number of isotopomers as the original collection. The identity of the original compound is confirmed by the fragmentation patterns resulting, and its acquired mobility information can contribute to this confirmation.

The absolute quantity of any compound can be determined by comparison if the quantity of any of the subsets of the collection is known. The use of a liquid chromatographic (LC) separation prior to the entrance of the ion collection reduces the number of ion collections that enter the IM channel at any given time, which can be helpful but is not needed. This technique can be used in the quantitative analysis of extremely complex mixtures, for instance, a tissue, cell, biopsy, or biofluid, human or non-human.

In such a case, an appropriate isotopomeric internal standard (IS), IROA or otherwise, that contains a multitude of the same compounds at a fixed or known concentration can be added to the biological material. The resulting pooled mixture can be analyzed and quantitated with complete confirmation of identities without the need for chromatographic baseline separation of the material as current practice requires.

A preferred embodiment of this method can include the preparation of the biological sample, addition of the isotopomeric mixture, separation of the pooled material; first by an high-performance LC (HPLC) separation, generally LC coupled to mass spectrometry (LC/MS), followed by an IM channel, and finally fragmentation by MS/MS. Other separation methods such as gas chromatography (GC), supercritical fluid chromatography (SFC), capillary electrophoresis (CE), or similar, or non-chromatographic systems such as Solid Phase Extraction (SPE) or on-line methods can also be used to help but are not needed. Any compound that is present in the IS can be quantitated at the level of the MS, or MS/MS. Identity is confirmed by MS/MS. See, e.g., Stupp, et al., *Anal. Chem.* 2013, 85 (24), 11858-11865.

Another aspect of the contemplated invention provides a new aspect to the previously discussed Phenotypic IROA Protocol. This aspect contemplates a reagent pair that is capable of transforming the biologically-produced metabolite compounds of a natural abundance mass spectral analysis sample into an IROA sample. This reagent pair comprises two reactively identical reagents that constitute first and second isotopomers.

The first isotopomers contain about 2 to about 10% of a first isotope, and second isotopomers contain about 90 to about 98% of a second isotope of the same atom. The first and second isotopes are stable to radioactive decay and are other than hydrogen and deuterium.

It is preferred that the reagent molecule contain 4 or more atoms that can be one or the other of the isotopes of choice. The upper limit of such atoms is typically a matter of convenience, with reagents that can contain 6 to 10 atoms of possibly variant isotopes of choice being preferred.

Each of the reagent pair contains the same reactive group that reacts with and bonds to a functional group of one or more compounds present in a composition of biologically-produced natural abundance metabolite compounds. Each of those metabolite compounds has a molecular weight of about 2000 AMU or less, preferably about 1500 AMU or less, and more preferably about 1000 AMU or less.

It is noted that the phrase "reactive group that reacts with and bonds to a functional group" is not chemically accurate in that once reacted with each other, the reactive group and the functional group are no longer in existence so they cannot bond to each other. Rather it is residues of each group that bond to each other. The latter phrase is thought to be cumbersome and therefore, the former, quoted, phrase is used with the understanding that the latter phrase more chemically accurate is intended.

The reactive group of the reagent pair reacts with and bonds to a functional group selected from the group consisting of one or more of an amine, aldehyde or ketone, hydroxyl, thiol and carboxylic acid. Those reactive functionalities are present in proteinaceous metabolites and also compounds containing sugars, as well as mostly oxidized carbonaceous condensation products such as the terpenoids such as limonene, carvone and geraniol.

A particularly preferred reactive group reacts with and bonds to an amine group as is present as the amino-terminus of oligopeptides, amino acids and compounds with exocyclic nitrogen atoms such as mescaline, serotonin, and dopamine.

One such particularly preferred reactive groups is an isothiocyanate group. Isothiocyanate synthesis is well known in the art such that an isothiocyanato group containing a desired percentage of 13C can be linked to a carbonaceous group that itself can be prepared to contain a desired percentage of 13C so that desired pares of isotopomers can be readily prepared. A particularly preferred isothiocyanate is phenylisothiocyanate (PITC).

In another preferred reagent pair, the reactive group reacts with and bonds to a ketone or aldehyde group. Here, reactive group is a hydrazine or a semicarbazine that forms a hydrazone or semicarbazide with a ketone or aldehyde of a metabolite. Syntheses of these reactive group-containing compounds is also well known so that they too can be linked to carbonaceous moieties that contain a desired amount of 13C.

The Problem and Problem Solved

It is possible to use metabolomic techniques, such as the IROA basic, or IROA phenotypic protocols (optimally), or standard metabolomic techniques to identify and crudely quantify several hundred or even thousands of compounds in a biological sample. However, until the present invention, in order to make such measurements and to compare the measurements from any two or more samples, all the samples needed to be analyzed in a single batch, ideally during a single day because day-to-day variances are too great to otherwise overcome, and absolute quantitation; i.e., relative to a known standard, cannot be assured.

It is currently not quantitatively acceptable to compare samples assayed on the same instrumentation several days apart, and impossible to compare data generated on different instruments, or based on different methods. Instrument drift, chromatographic drift, and even environmental conditions can alter results sufficiently so that reproducibility is hard to obtain even on the same instrument.

In addition to these problems of quantitation, the identification of any compound across many mass spectral techniques alone is unlikely to be successful unless very careful calibrations have been made and authentic standards are run. This is because, not only are there multiple biological compounds that can be confused because they have the same exact mass but, even more problematic, there are often more artefactual or fragmentary compounds that are structurally different from, but can share the correct mass, or even formulae, as biological isobaric equivalents. The IROA workflow directly addresses these issues, and others, on many levels and overcomes them.

The IROA workflow provides a "standard sample", referred to as "the Matrix sample", that is deeply analyzed multiple times during the analytical session. The Matrix sample is randomly intermingled with experimental or clinical samples. The identity and behavior of the compounds in this Matrix sample are used to identify all of the same compounds in the experimental samples based on their shared IROA patterns. There can be different Matrix sample types for different analytical situations; i.e., a "Matrix" for Blood plasma, a "Matrix" for human liver, or even a "Matrix" for wheat. The Matrix sample can contain synthetic IROA patterns in situations as described in IROA963, IROA964, and IROA251.

A Matrix sample is always constituted as the same carefully controlled mixture of compounds. Different compounds can be present at different concentrations; however in any given "Matrix" batch, each individual compound is always present at the same concentration in all aliquoted Matrix samples. All the compounds present in the Matrix sample are highly defined.

The Matrix sample is a Basic IROA sample, and thus every compound is equally present at both predetermined isotopomeric balances, such as the preferred 5% C13 and 95% C13. This means that the IROA peak shape for each compound ideally is comprised as a perfectly balanced, symmetrical collection of peaks, with each half a mirror image of the other.

Because of the symmetry of the IROA peaks in the Matrix, Matrix samples can be completely catalogued; even peaks deep into mass spectral noise at extremely low levels well below what would otherwise be possible to discern can be identified and characterized. The triple-redundancy of the Basic IROA peak guarantees the consistent interpretation, and identification in every analysis.

Because all the compounds present in the Matrix samples can be catalogued, and because they are consistent in a given Matrix, their chromatographic behavior, ionization efficiency, ion mobility (IM) characteristics, fragmentation behavior, and the like can be evaluated and these values are used to correct for any day-to-day variances, when the analytical system is similar, or even if it is very dissimilar.

Because the majority of these compounds are found even across very different analytical platforms; i.e., with different chromatographic, ionization, or detection systems, the IROA characteristics of the IROA primary scan and the IROA secondary chemical characteristics, as seen in ion mobility, SWATH [see, Gillet et al., *Mol Cell Proteomics*, 11:011.016717 (Jun. 1, 2012)], or other fragmentation systems assure that every compound in Matrix can be mapped from any analytical system to any other analytical system, thereby providing a mechanism for directly comparing the complete Matrix chemical composition of any two matrix samples, and through them any clinical or experimental samples they support.

A Table illustrating windowing widths for SWATH set to pass all of the desired IROA compound peaks through them is shown below.

| Max # carbons below center | center | window | overlap | count | min | max |
| --- | --- | --- | --- | --- | --- | --- |
| 3 | 59 | 10 | 5 | 1 | 49 | 69 |
| 4 | 74 | 15 | 8 | 2 | 59 | 89 |
| 5 | 89 | 15 | 8 | 3 | 74 | 104 |
| 7 | 119 | 30 | 15 | 4 | 89 | 149 |
| 9 | 149 | 30 | 15 | 5 | 119 | 179 |
| 13 | 209 | 60 | 30 | 6 | 149 | 269 |
| 17 | 269 | 60 | 30 | 7 | 209 | 329 |
| 27 | 389 | 120 | 60 | 8 | 269 | 509 |
| 36 | 509 | 120 | 60 | 9 | 389 | 629 |
| 54 | 749 | 240 | 120 | 10 | 509 | 989 |

Figure 12A:
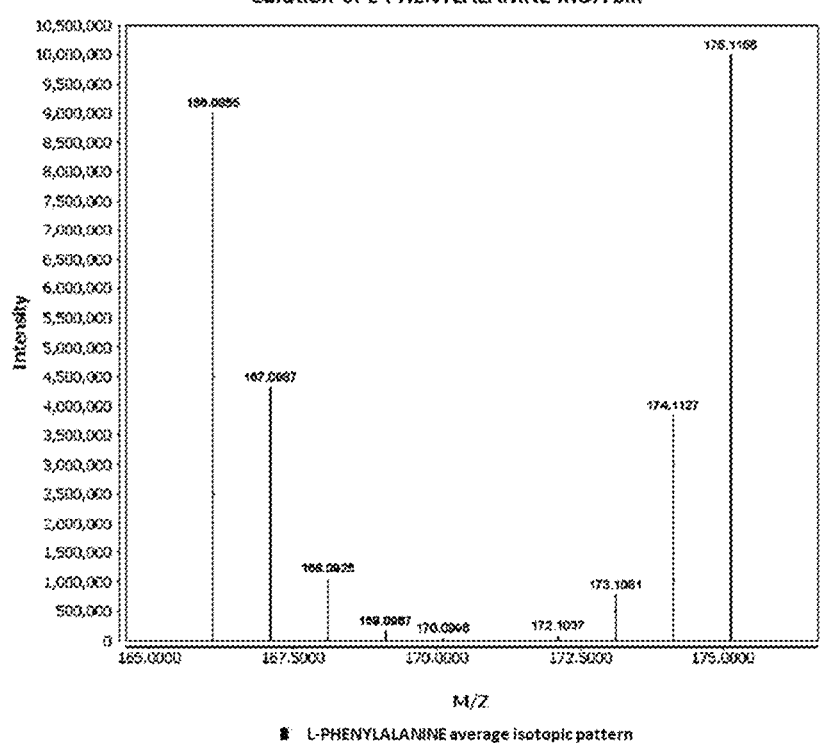
FIG. 12A illustrates the mass spectral IROA peak pattern for phenylalanine based on use of a mixture of equal amounts of 5% C12 and 95% C13 phenylalanine and 95% C12 and 5% C13 phenylalanine.
Figure 12B:
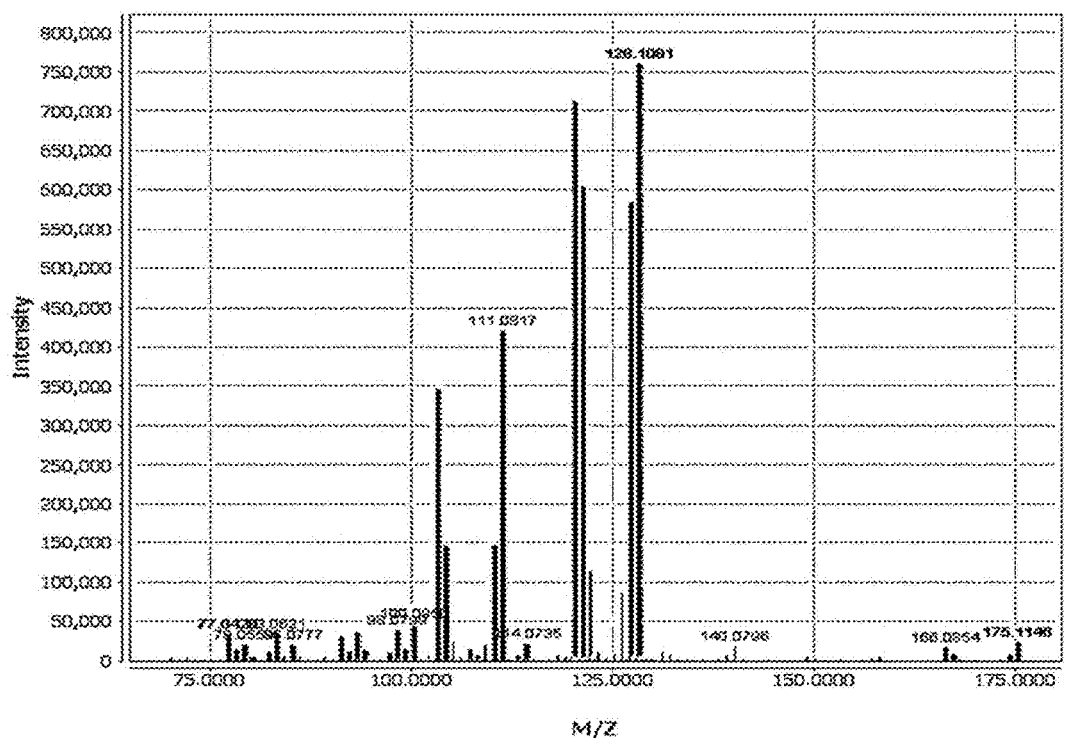
FIG. 12B illustrates the mass spectral IROA peak pattern for that same phenylalanine sample after SWATH fragmentation.
Figure 13A:
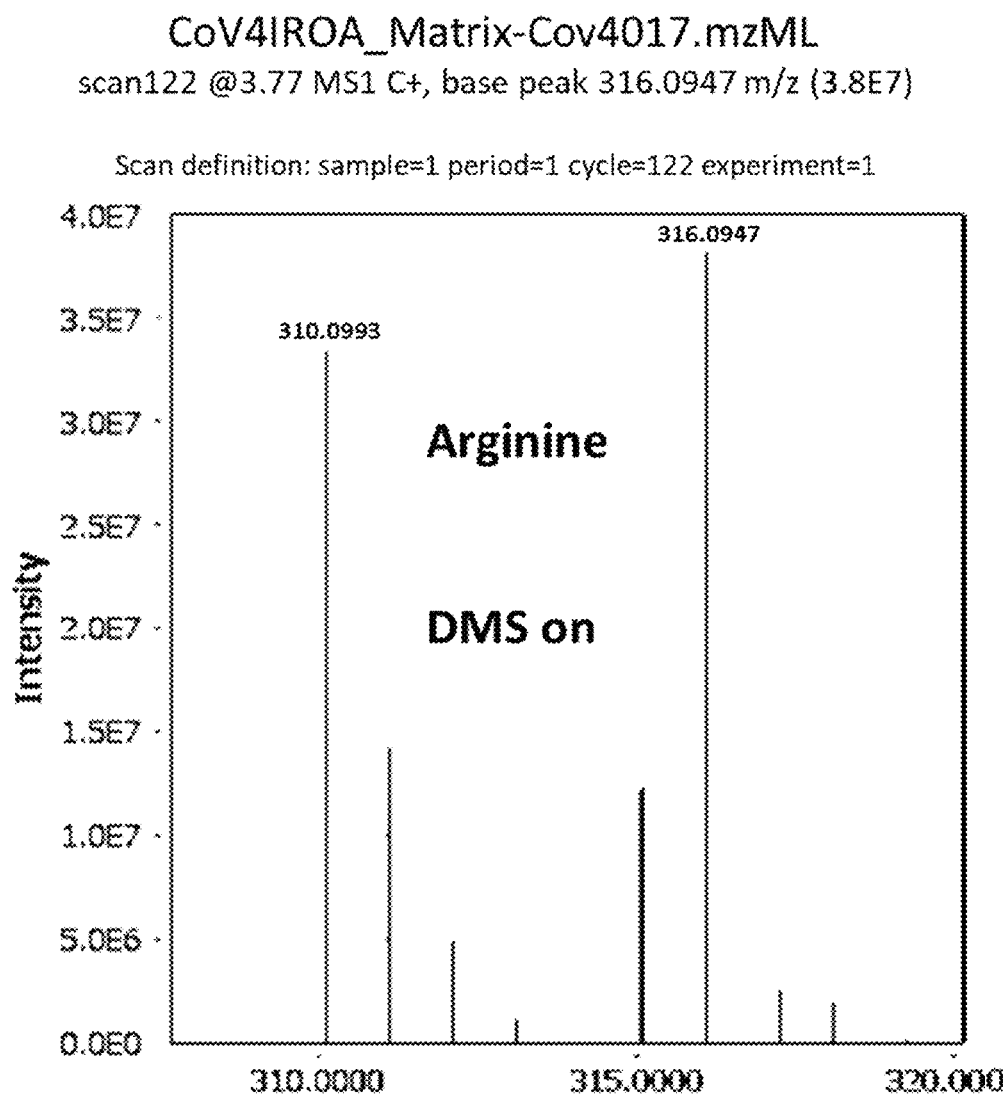
FIG. 13A and FIG. 13B illustrate that derivatized peaks of arginine maintain their IROA character in ion mobility [with and without differential mobility spectrometry (DMS)] when derivatized using either isotopically labeled IROA compounds (FIG. 13A) or with natural abundance compounds derivatized with isotopically labeled reagent such as a 95% C13 phenylthiocarbamyl (PITC) group (FIG. 13B). The collection of isotopomers appear as a unit in Ion Mobility, here Sciex SelexIon™.
Figure 13B:
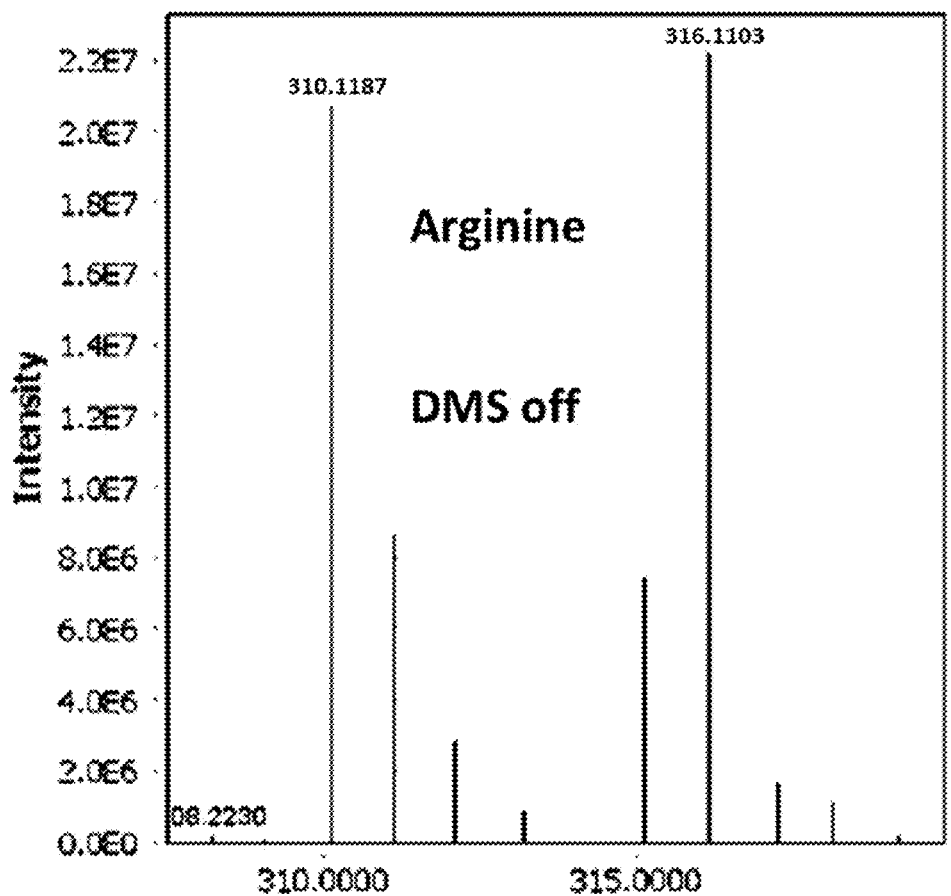
Figure 14A:
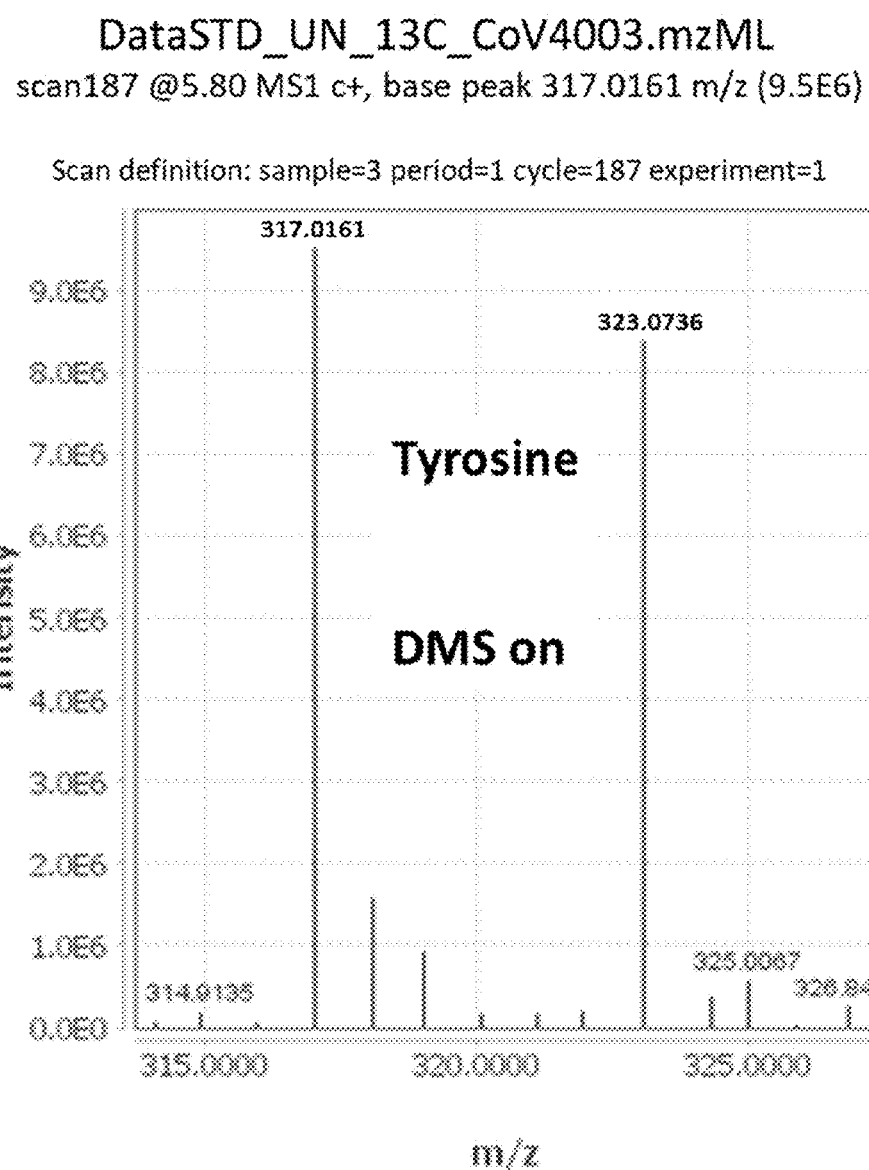
FIG. 14A and FIG. 14B illustrate a similar maintenance of IROA character for similarly prepared and assayed tyrosine derivatives.
Figure 14B:
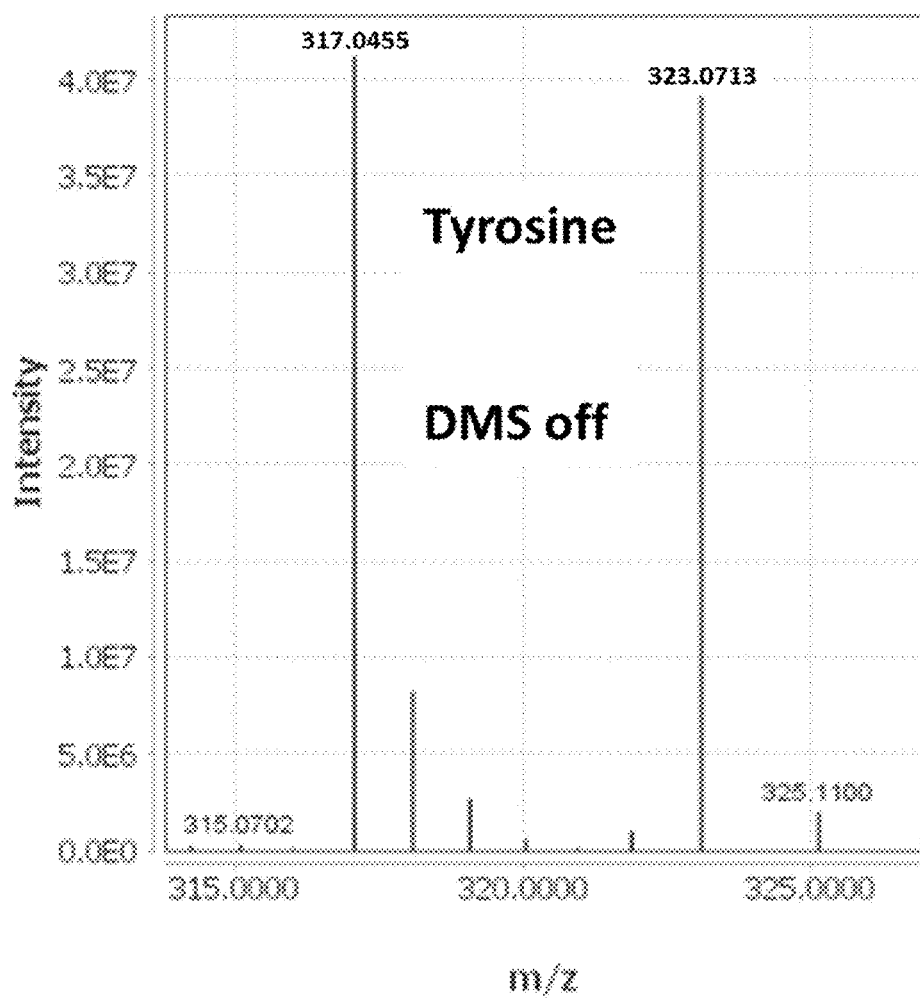
Figure 15A:
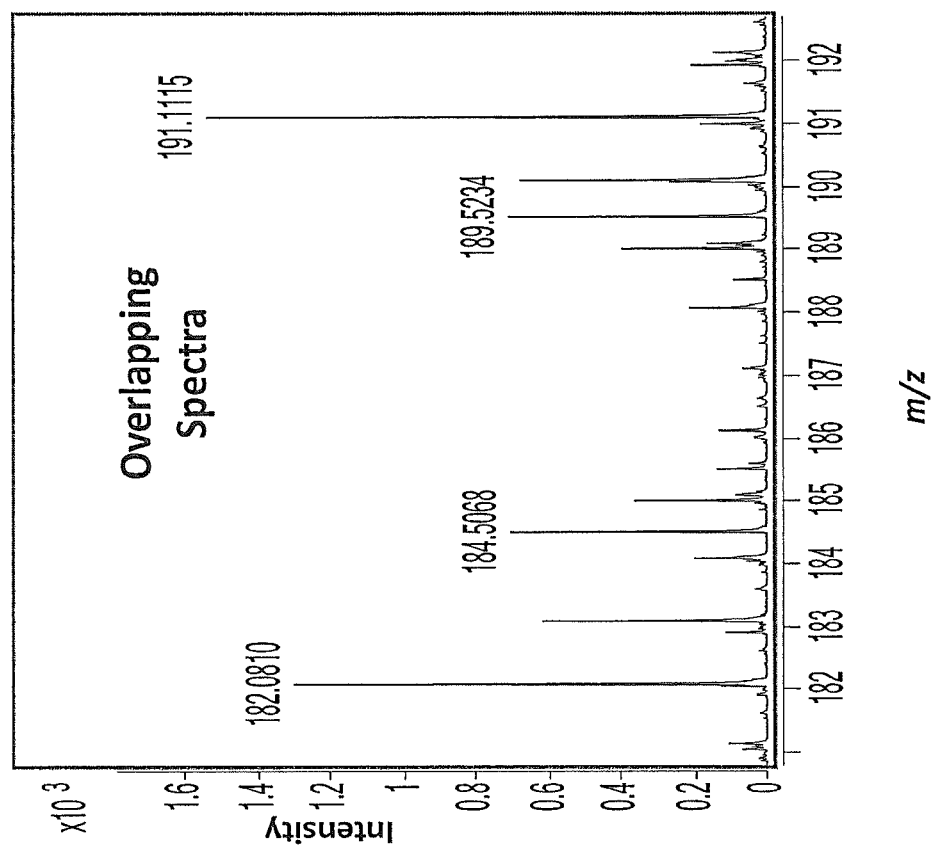
FIG. 15A, FIG. 15B, FIG. 15C and FIG. 15D illustrate the power of IROA, particularly in conjunction with ion mobility to separate complex spectra into their component individual spectra. Thus, the isotopomeric collections of IROA peaks remain IROA peaks in IM, here using an Agilent 6560 (ion mobility time of flight) IM-QTOF machine, that uses Drift Tube IM (DT-IM). Although the ClusterFinder™ software separates out overlapping IROA peaks based on mass differences in the pre-IM Mass spectrum (FIG. 15A) here two co-eluting IROA peaks are separated cleanly in the IM (FIG. 15B) for complete compound spectral identification (FIG. 15C and FIG. 15D) based on their IROA characteristics.
Figure 15B:
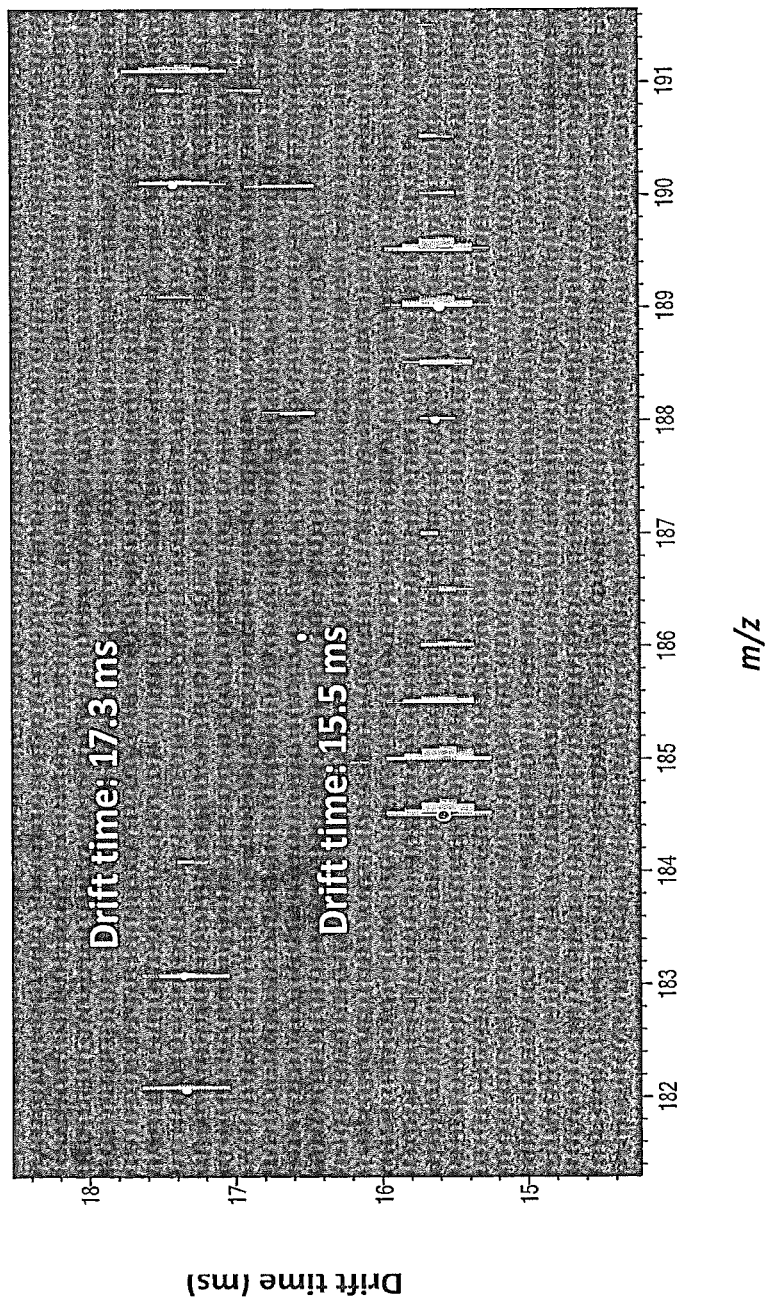
Figure 15C:
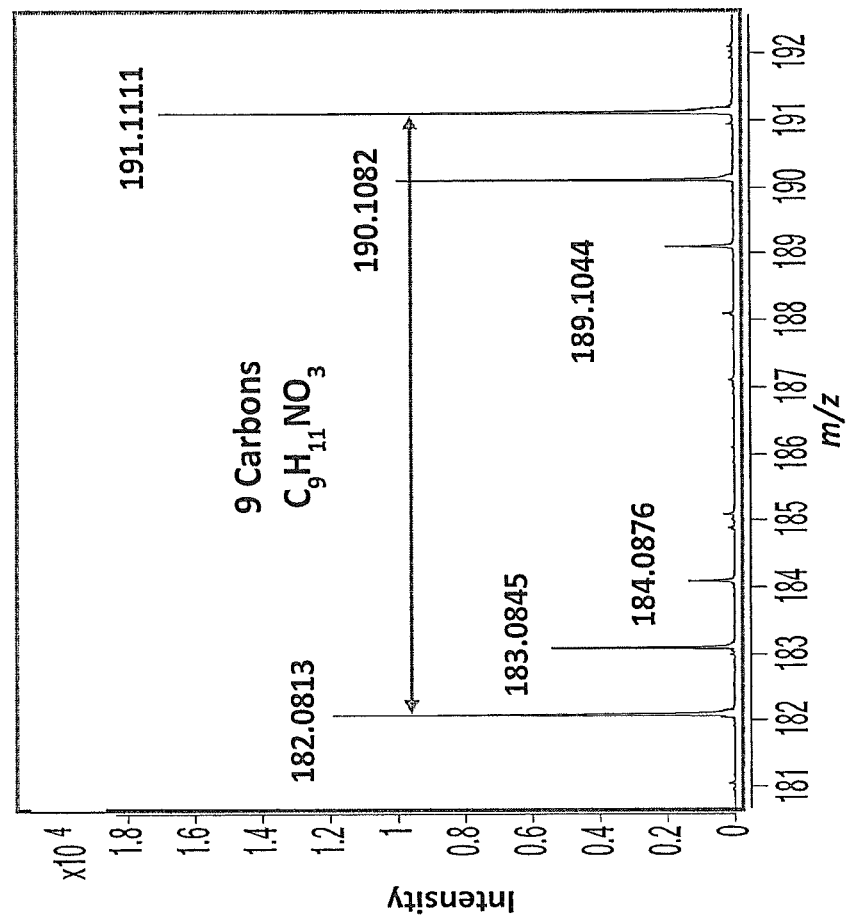
Figure 15D:
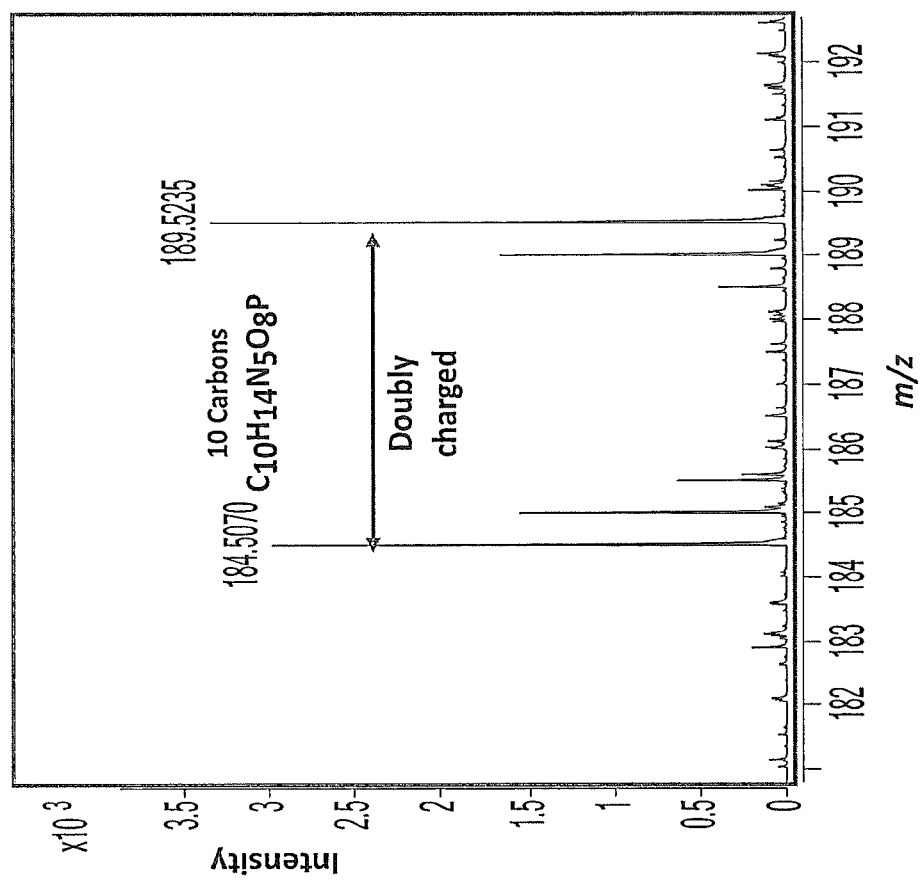

Windowing schemes such as SWATH windows set as shown above permits all IROA peaks to passage through them to provide for the isolation of a complete IROA peak set pattern as is shown in FIG. 12A. It is based on the maximum number of carbons in any known metabolite with a mass of the center mass, and sets windows (minima and maxima), and overlaps accordingly. FIG. 12B illustrates the phenylalanine fragmentation pattern that provides diagnostic structural information as seen from FIG. 12C.

Because the chemical makeup and therefore chromatographic behavior of the Matrix sample is identical to the Internal Standard applied to the Experimental samples and analyzed within the same batch, it is possible to use the in-depth, informationally-strong, triply redundant chemical identification information obtained from the Matrix sample and apply it to the Experimental samples.

The Matrix samples can be analyzed to find, identify, and collect all identifying physical characteristics for all of the compounds contained within it with extreme accuracy and sensitivity. For every triply redundant IROA peak, the physical information can include but is not limited to information from the primary ms scans:
  the retention time (RT), 12C monoisotopic mass, 13C monoisotopic mass, number of carbons contained in the molecule;
  in-source and post-source fragmentation characteristics;
  any physical characteristics gleaned from other methods applied to the effluent stream, for instance, IR, UV;

various post source fragmentation methodologies, including for instance, collision-induced dissociation (CID), electron-capture dissociation (ECD), SWATH, etc., whether Directed (data dependent acquisition-DDA), Independent (data independent acquisition (DIA), such as MSe, SWATH, etc., ion mobility (IM);

or any other technique that can provide information to support the identification of this IROA peak.

The experimental or clinical samples are biochemically complex and contain a diverse assortment of compounds; however, the carbon isotopic balance for these compounds is present only at natural abundance C13 levels; i.e., approximately 1.1% C1.

An internal standard (IS) that is identical in concentration and chemical composition to the 95% C13 (or other suitable) isotopomeric portion of the Matrix samples is added to each clinical sample. This addition means that each experimental sample can be analyzed as a Phenotypic IROA sample because it now conforms to the Phenotypic IROA protocol.

Because the same C13 isotopomeric IROA signal is present in both the Matrix and Experimental samples, and the chromatography is consistent across both, the chemical compound identification and physical characteristics seen, and verified, in the Matrix can be mapped directly to the experimental samples. Because of the uniqueness of the IROA signal in the IS placed into a redundant Phenotypic sample, the mapping does not require that the experimental samples also have the secondary physical characteristics, but rather the user can infer those secondary physical characteristics based on reference to a co-incidentally analyzed Matrix sample.

The Matrix and experimental samples are randomly interspersed into a single sample set (for instance, such that there is one Matrix injection for every approximately 10 experimental injections), and the entire sample-set analyzed.

Because the samples have been completely and randomly intermixed during the analysis, the catalog of all peak pairs, their RT, number of carbons, IM and fragmentation characteristics provide information where each of these same IROA peaks is found in the experimental samples. The Natural abundance peak is easily located and quantitated as it collocates with it's IROA peak at a mass that is the mass of the IROA-C monoisotopic peak less the number of carbons it contains times the mass of a neutron.

Quality Control, reproducibility, and accuracy for all samples analyzed according to the IROA workflow are assured because:

the Matrix sample is a "standard" sample, that is always the same, the catalog of all IROA peaks found in each daily Matrix analysis provides a way to quantitate the performance characteristics for the instrumentation for every day's analysis and provides a mechanism for correcting any instrumental error or determining that the error on a given day was un-acceptable;

the amount of IS introduced to every sample is identical to that in the Matrix and is the same across all samples, the sum of all signals in the IS is a constant and can be used to normalize samples if they are not otherwise normalized.

With the inclusion of an orthogonal, second-stage analysis and the collection of data detailing additional physical characteristics, such as an ion mobility, fragmentation, such as SWATH, UV, or IR, etc., the compounds found in two sets of Matrix samples that have been analyzed under very different analytical conditions can be unequivocally mapped from one to the other and therefore provide for the quantitative comparison of the clinical or experimental samples associated with their respective Matrix samples.

This workflow can be automated in its entirety due to the triple-redundancy of the compounds in Matrix samples, and the redundancy and equivalency of the clinical samples.

Thus, the IROA workflow combines the strengths of two IROA-based protocols to 1) provide a method for the quantitation of a very large number of compounds to be measured in a single analytical run, 2) provide a mechanism to correct any errors in quantitation irrespective of the analytical systems used, and 3) provide a mechanism to assure that the identification of all compounds is consistent across time and analytical platforms.

The Phenotypic IROA Protocol

The Phenotypic IROA protocol is a protocol for situations in which it is not feasible or practical to label the experimental sample itself but a common and consistent 95% (+/−3%) IROA internal standard, such as the above described C13-IS, is used to assure accurate identification of a molecule and accurate quantitation. The Phenotypic Protocol is useful for the analysis of human (clinical) samples, agricultural samples, industrial samples, or other situations where the size or the source of the experimental samples is such that it is simply not feasible to label them. However, the Phenotypic protocol, by providing a common rigorous IROA internal standard, provides a more accurate route for the identification and quantification of a large number of compounds that are found in the sample natural abundance isolates.

Unlike the "unbiased" or "non-targeted" analysis of basic IROA, Phenotypic IROA is a targeted quantitative analysis of a very large number of compounds based on a very chemically complex IROA internal standard (IS). A C13-IS can contain well over 1000 compounds (potentially unlimited), but the IROA properties outlined earlier do not require complete chromatographic separation to assure both the identity and quantitation of all the compounds contained in the IS.

The Phenotypic protocol puts an IROA internal standard into every natural abundance sample and uses the dual pieces of information from the C13-IS, 13C-monoisotopic mass and number of carbons, to locate the natural-abundance isotopomer of the same compound. Correlation of the natural abundance time-resolved chromatographic profile of the found peak, and it's natural-abundance isotopic form are then used to support the IROA-based identification.

Figure 5:
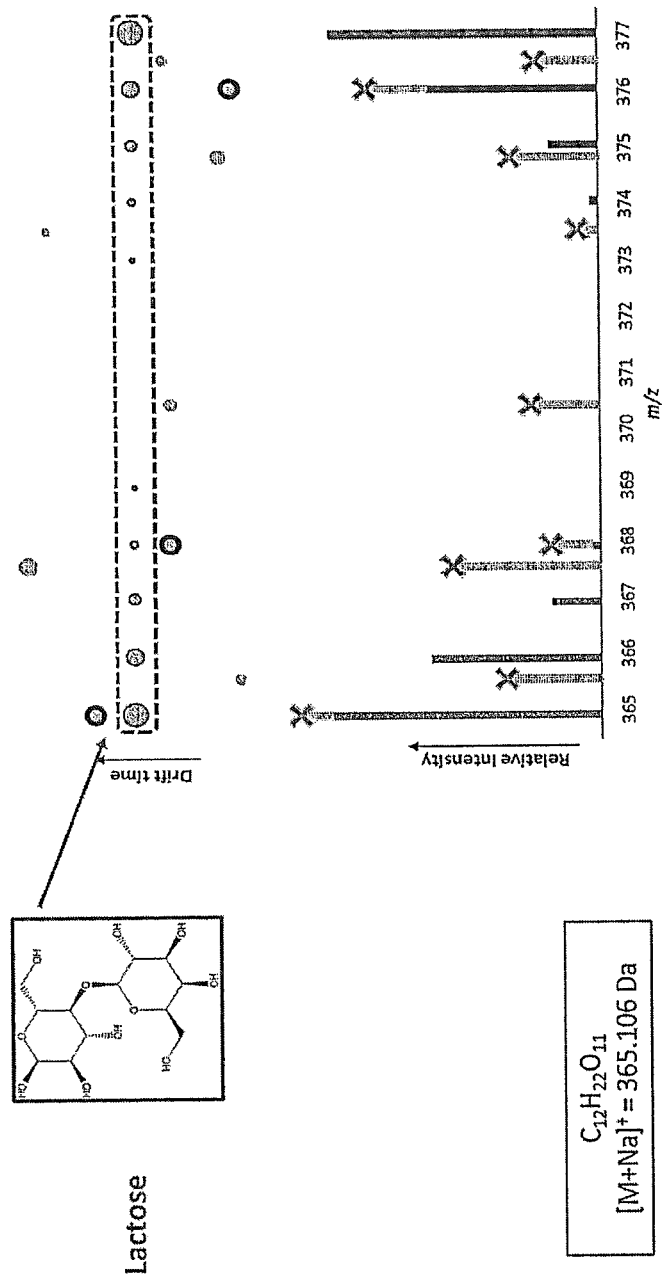
FIG. 5 whose upper portion shows a schematic of a IM apparatus drift tube with the analyte ions within the dashed rectangle and ions of unknown origin outside of that dashed rectangle and a simulated ion mobility spectrometric- (IMS-) Assisted IROA mass spectrum containing peaks with added X's above them to indicate the peaks due to those ions of unknown origin, and in which ions of unknown origin that interfere with detected IROA masses but have been separated by ion mobility are represented with black circles.
Figure 6:
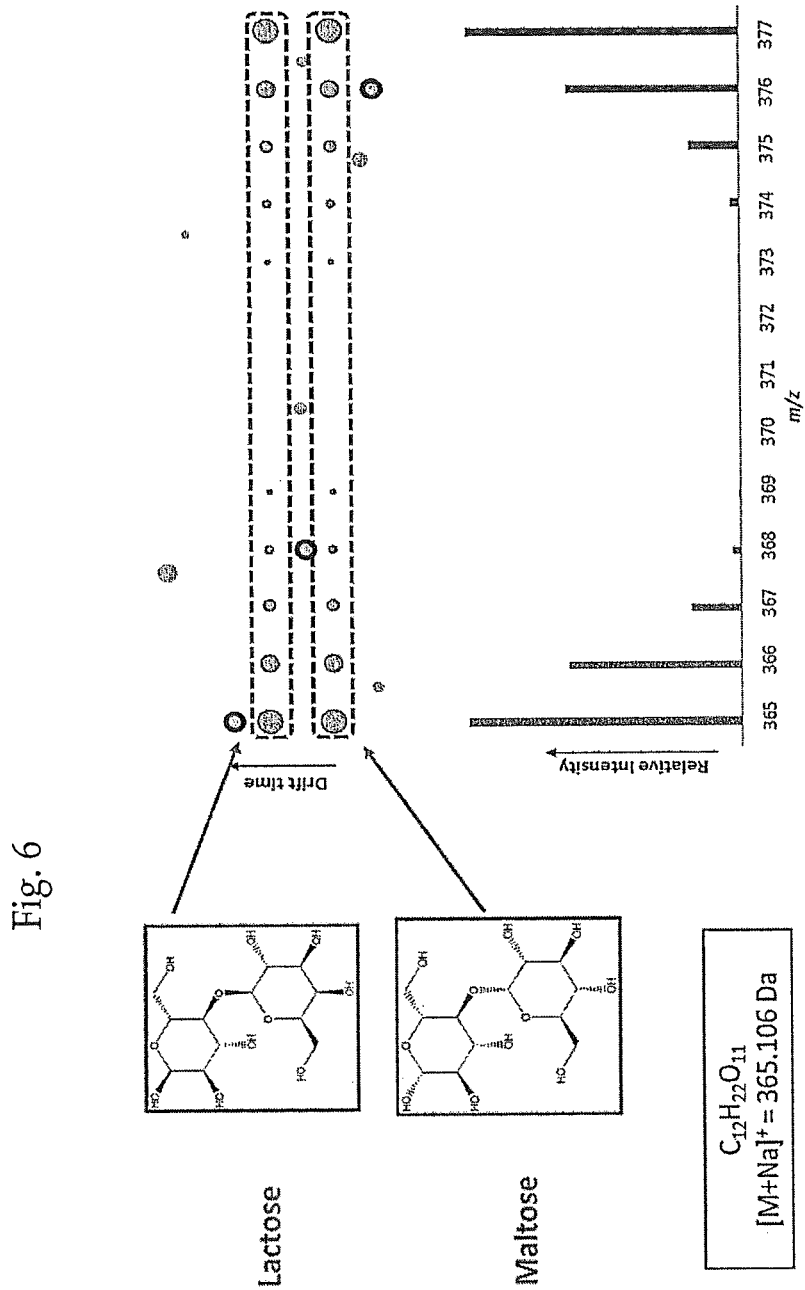
FIG. 6 is similar to FIG. 5, except that this figure is a simulation in which two isomers are detected and as seen in the upper schematic IM drift tubes whose separated analytes are shown within the two dashed rectangles and ions of unknown origin outside of those dashed rectangles with the same meanings as in FIG. 5, and because there are IROA internal standards for them, they can be independently quantitated, which would not be possible without both the IROA internal standards and ion mobility. See, e.g., Dwivedi et al., *Int. Journal Mass Spectrom.* 2010, 298 (1-3):78-90 that discusses use of IMS-assisted mass spectroscopy.
Figure 7A:
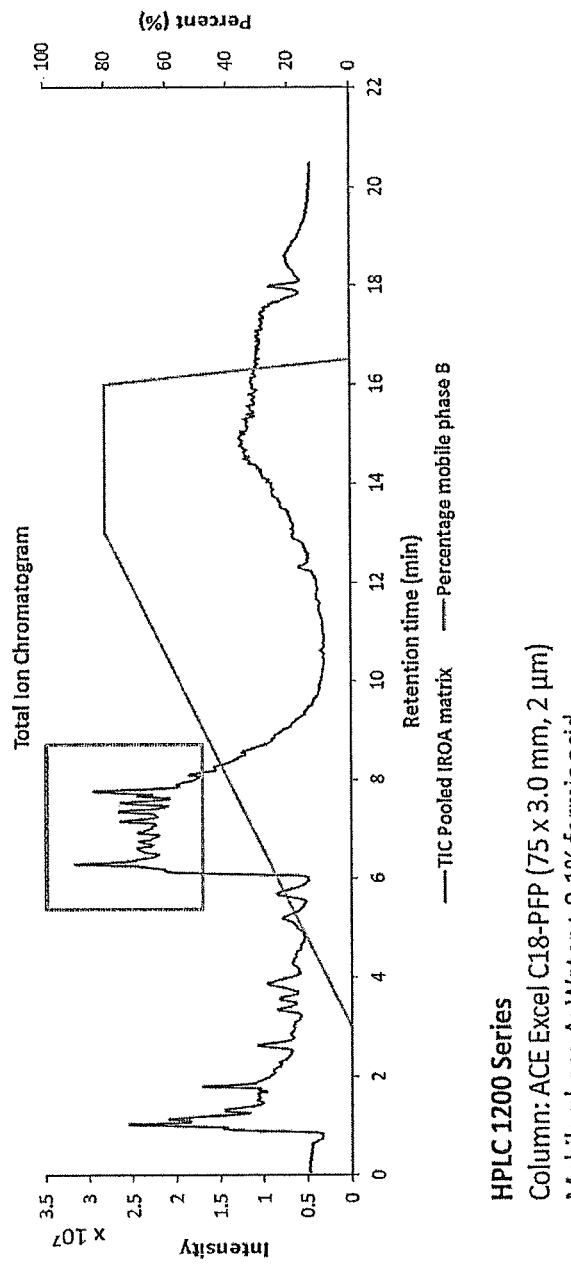
FIG. 7A illustrates a LC-IM-MS analysis of a portion of the pooled yeast extract (IROA Matrix) prepared as discussed in FIG. 4 and in greater detail hereinafter, in which the portion of the LC separation within the box is the portion analyzed mass spectrally and the line beneath the boxed line illustrates the elution solvent gradient.
Figure 7B:
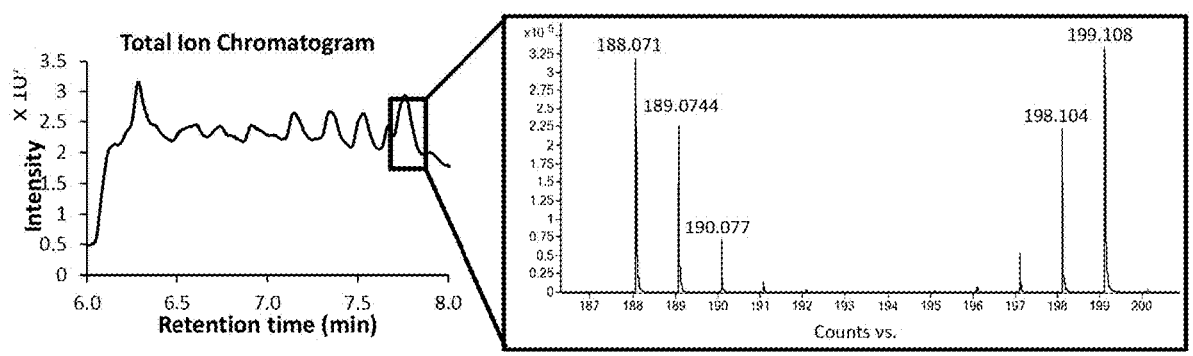
FIG. 7B illustrates a portion of the LC separation that was analyzed (boxed peak) with the resulting mass spectrum for an 11 carbon compound adjacent to the LC trace.
Figure 7C:
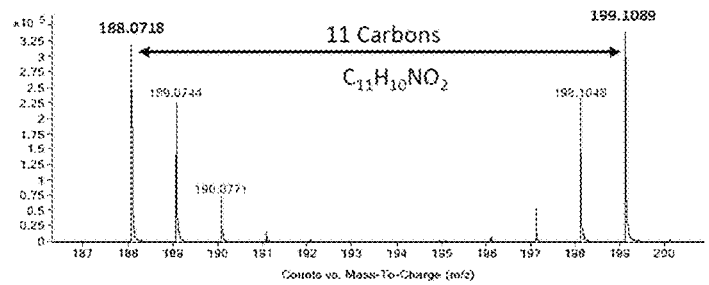
FIG. 7C illustrates further details of the separation and MS analysis in the upper portion such as retention time, mass range and drift time, as well as IM analysis readily showing the IROA peak pattern, specific drift time and number of carbons in the analyzed compound.
Figure 7C:
Figure 8A:
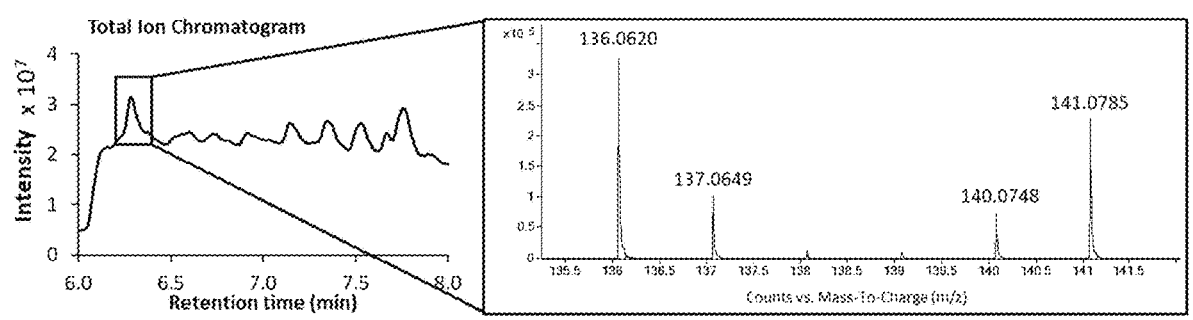
FIG. 8A illustrates a LC-IM-MS analysis of another peak (boxed) from a LC separation in which a 5 carbon compound was the analyte.
Figure 8B:
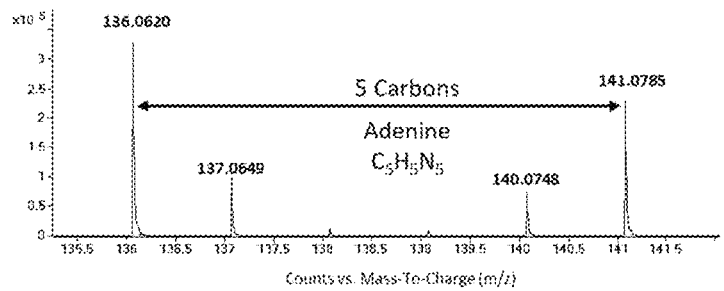
FIG. 8B illustrates one IROA recognized pattern using LC-MS separation with further details that indicate that two compounds are present from the IM data.
Figure 8B:
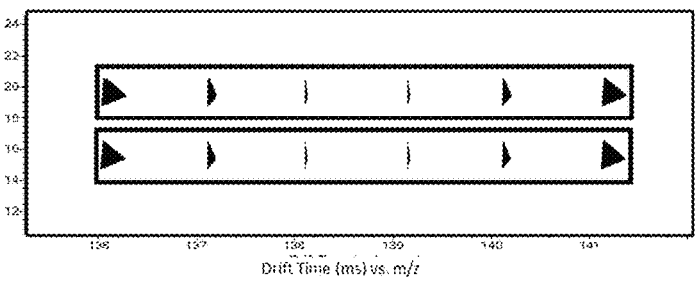
Figure 9A:
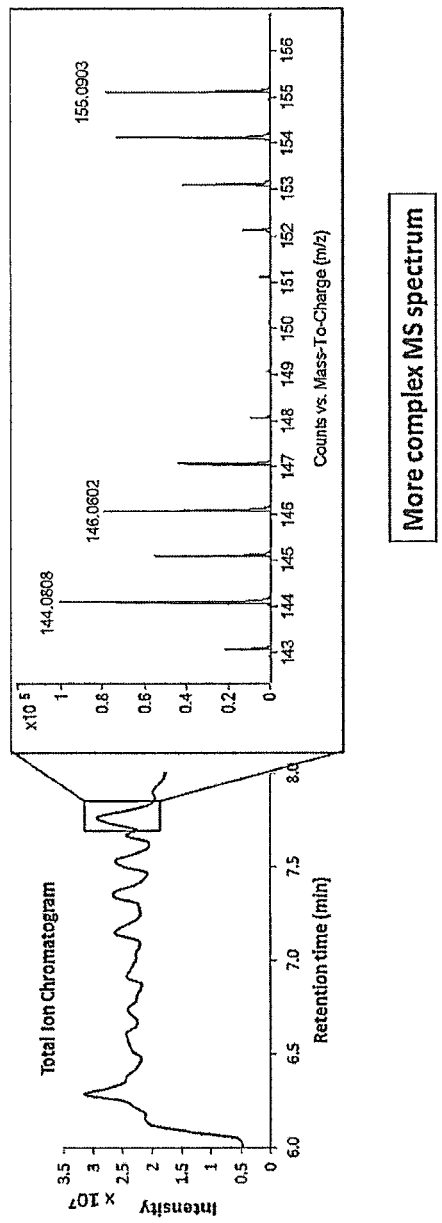
FIG. 9A illustrates an overlapping MS peak pattern in compounds obtained from the boxed LC peak on the left side of the figure.
Figure 9B:
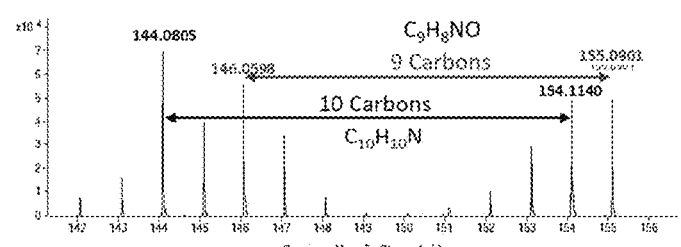
FIG. 9B illustrates the deconvoluted spectra in which the IM data indicate that two nine carbon compounds have the same chemical formula, and drift times matched with identity data reference libraries and that a ten carbon compound was also present.
Figure 9B:
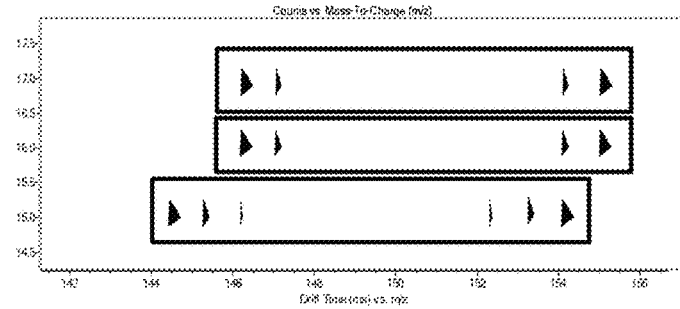
Figure 9C:
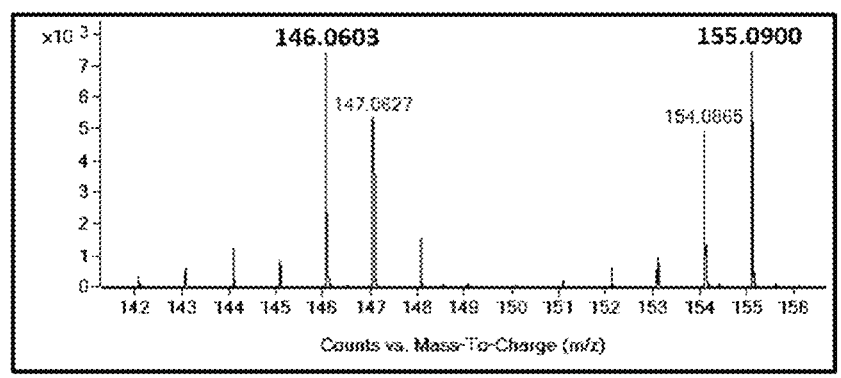
FIG. 9C shows the mass spectra for each of the three compounds identified.
Figure 9C:
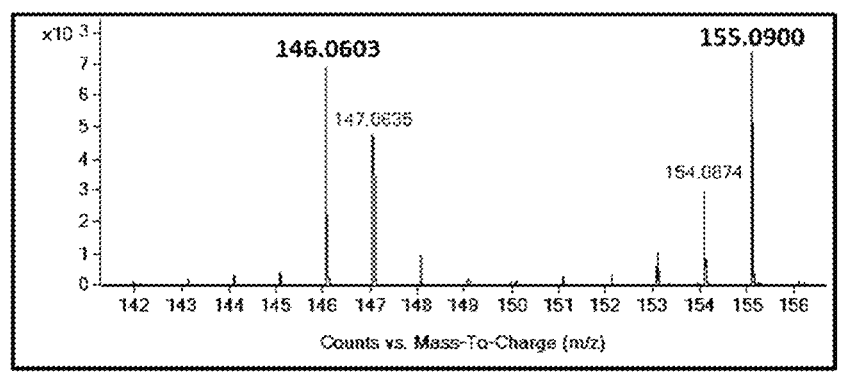
Figure 9C:
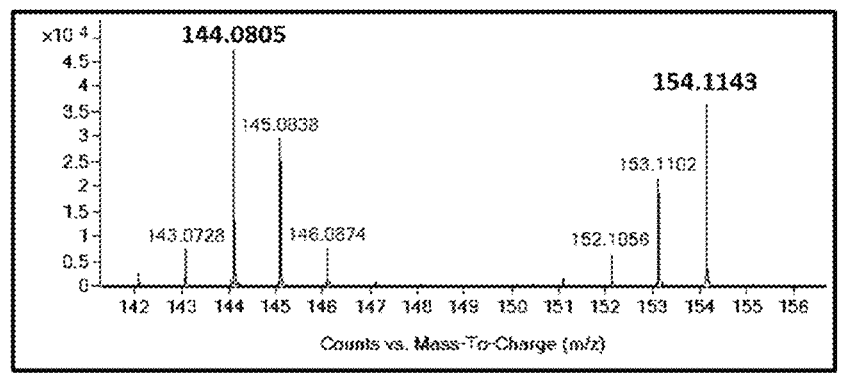
Figure 10A:
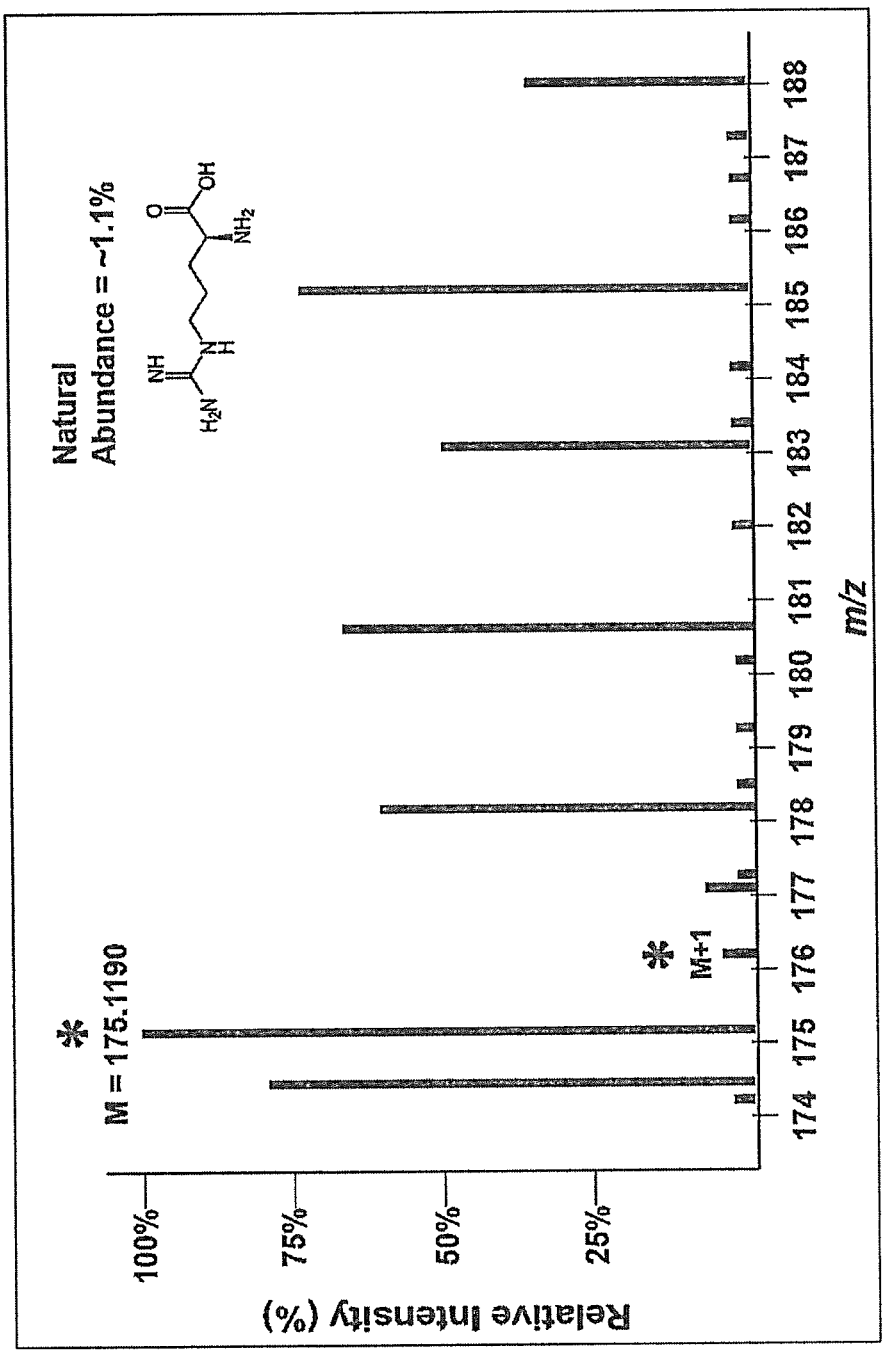
Figure 10B:
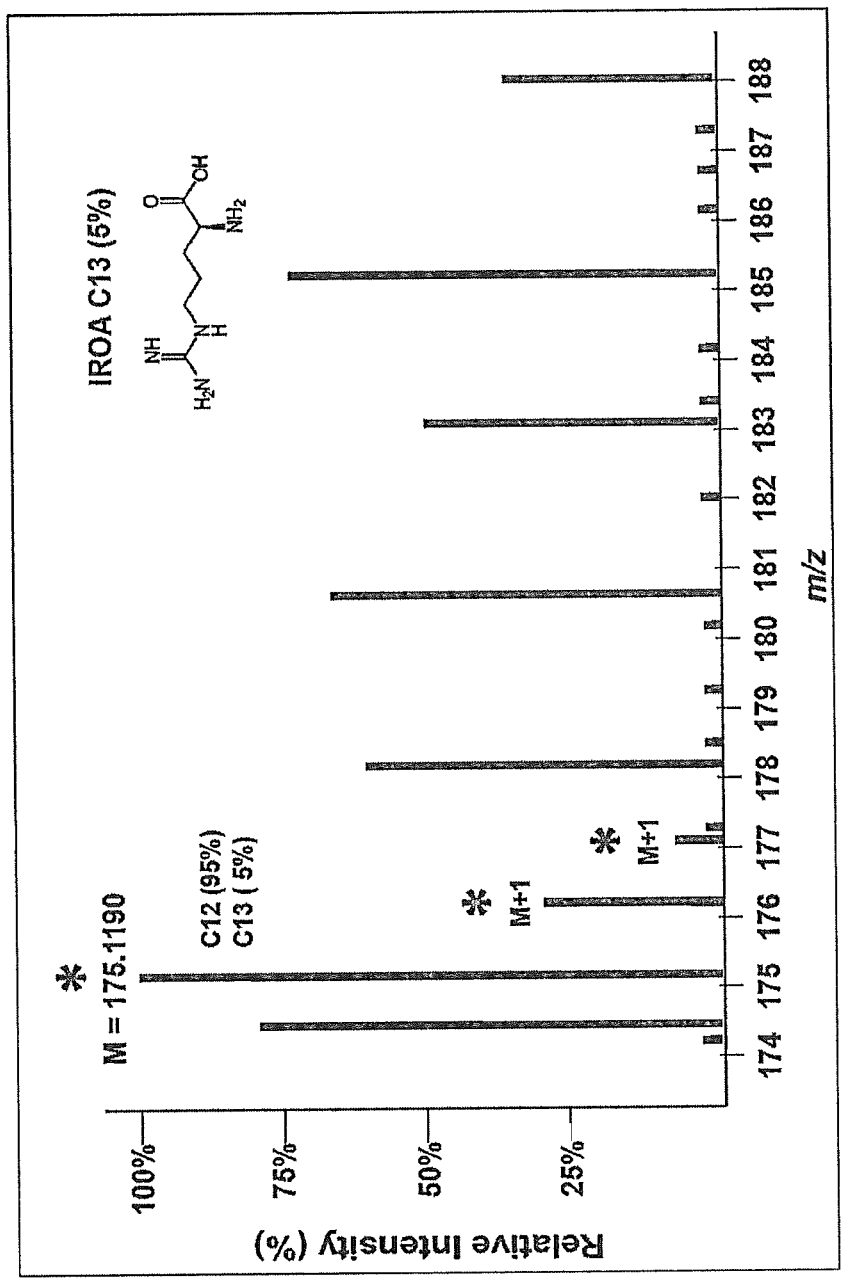
FIG. 10B shows the similar spectrum using arginine that contains 95% C12 and 5% C13.
Figure 10C:
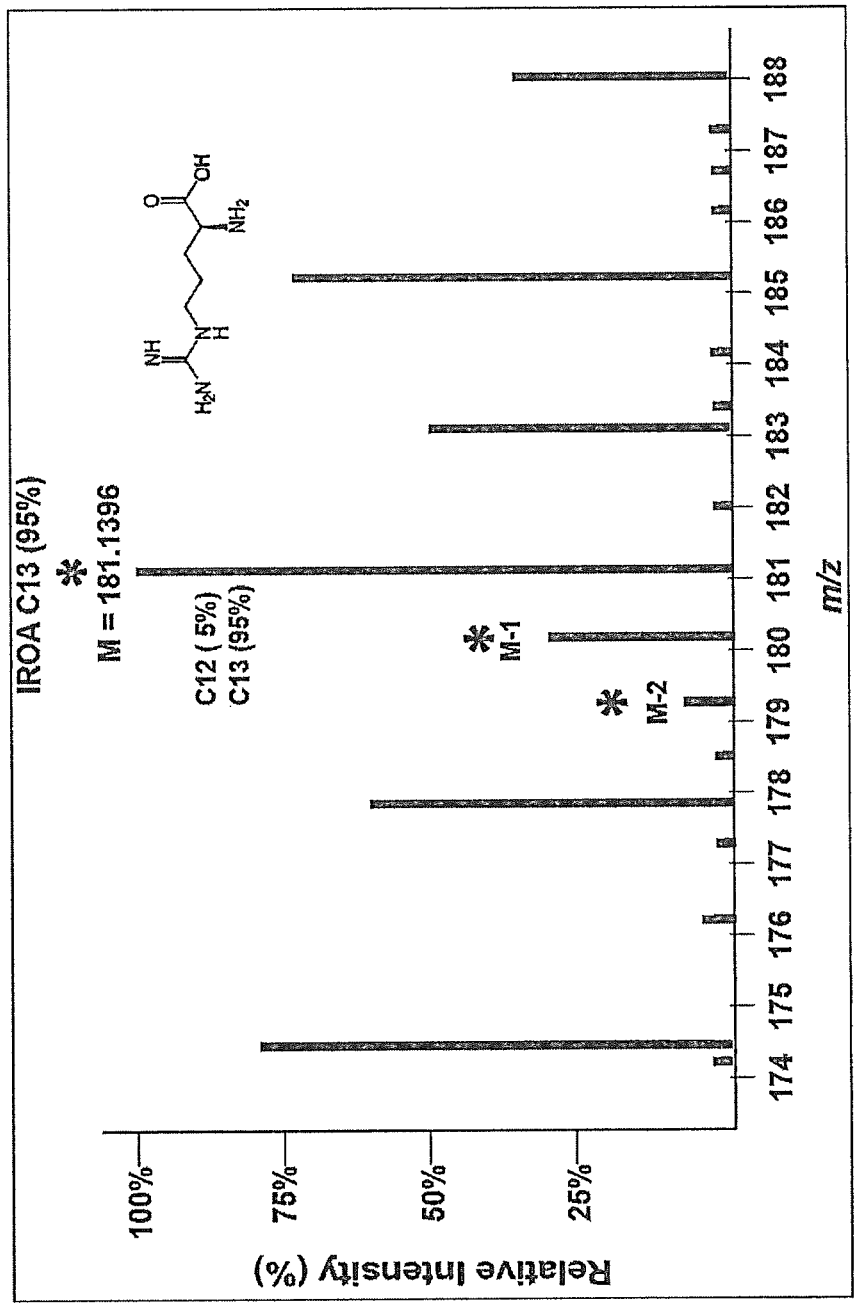
FIG. 10C shows the mass spectrum for arginine that contains 95% C13 and 5% C12.
Figure 10D:
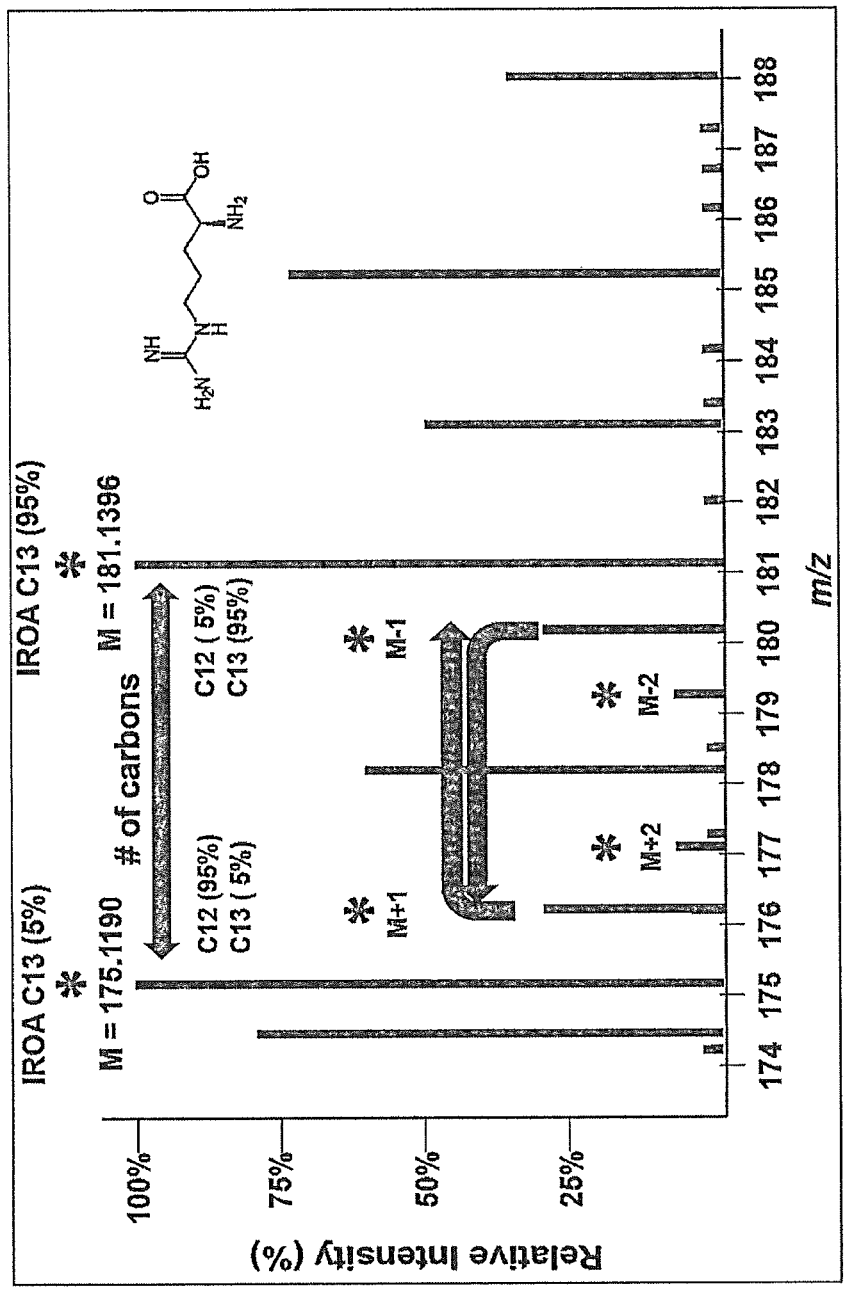
FIG. 10D shows the basic IROA spectrum of arginine when equal amounts of the compound containing 95% C12 and 5% C13 and the compound 95% C13 and 5% C12 are present.
Figure 10E:
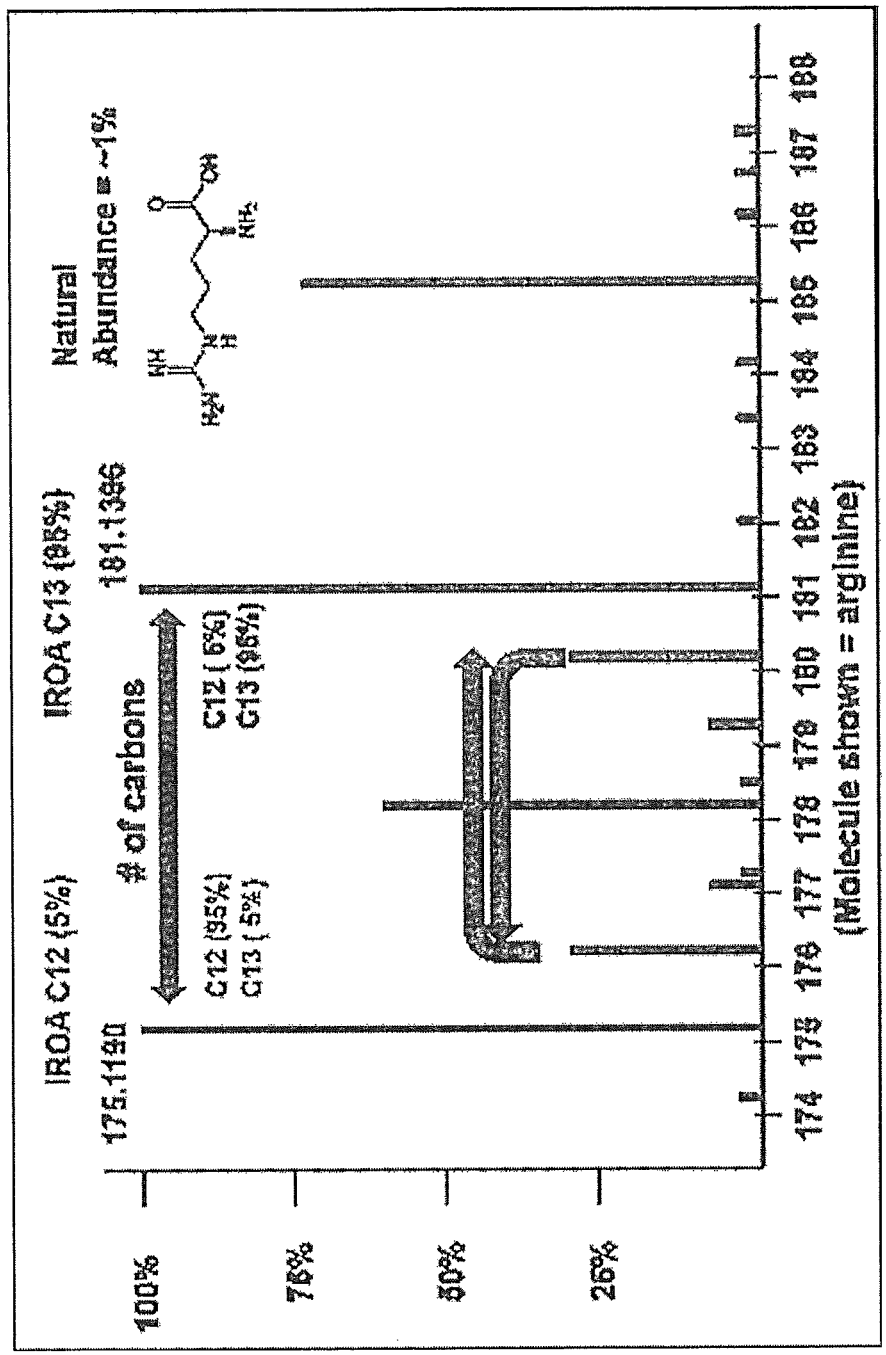
FIG. 10E illustrates triply redundant IROA peak patterns for arginine natural abundance noise in which relationship between the monoisotopic peaks is assured when the height of the C12 M+1, the C13 M-1, and the mass difference between the two monoisotopic peaks all indicate the same number of carbons are present in the molecule.
Figure 10F:
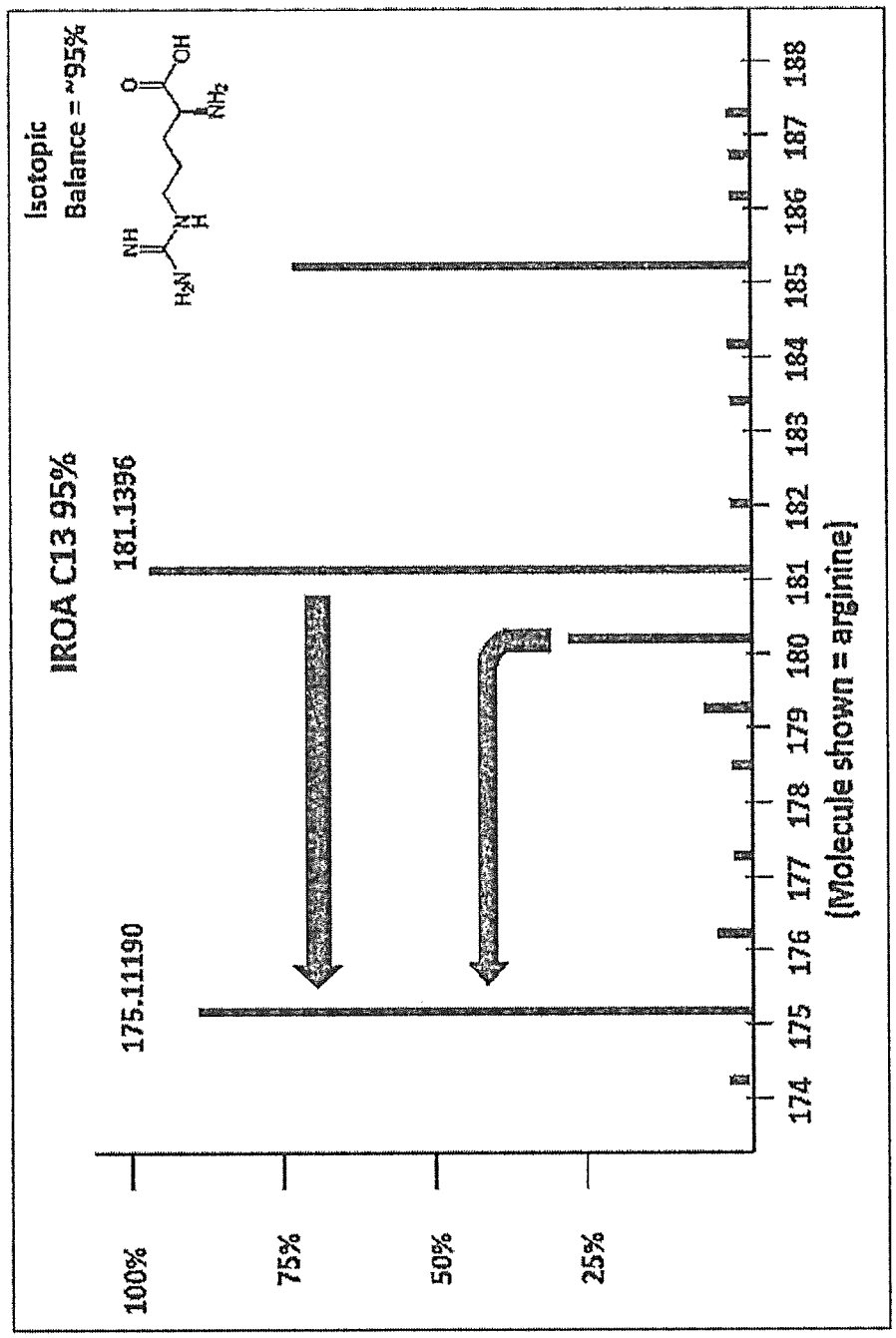
FIG. 10F illustrates Phenotypic "redundancy", in which the identity of the natural abundance peak is confirmed by both the molecular formula of the 13C monoisotopic peak and the number of carbons indicated by the height of it's M-1 provided by admixture of the C13-IS sample to the sample for analysis. Peaks associated with arginine are starred (*) in each spectrum of FIGS. 10A-D.
Figure 11A:
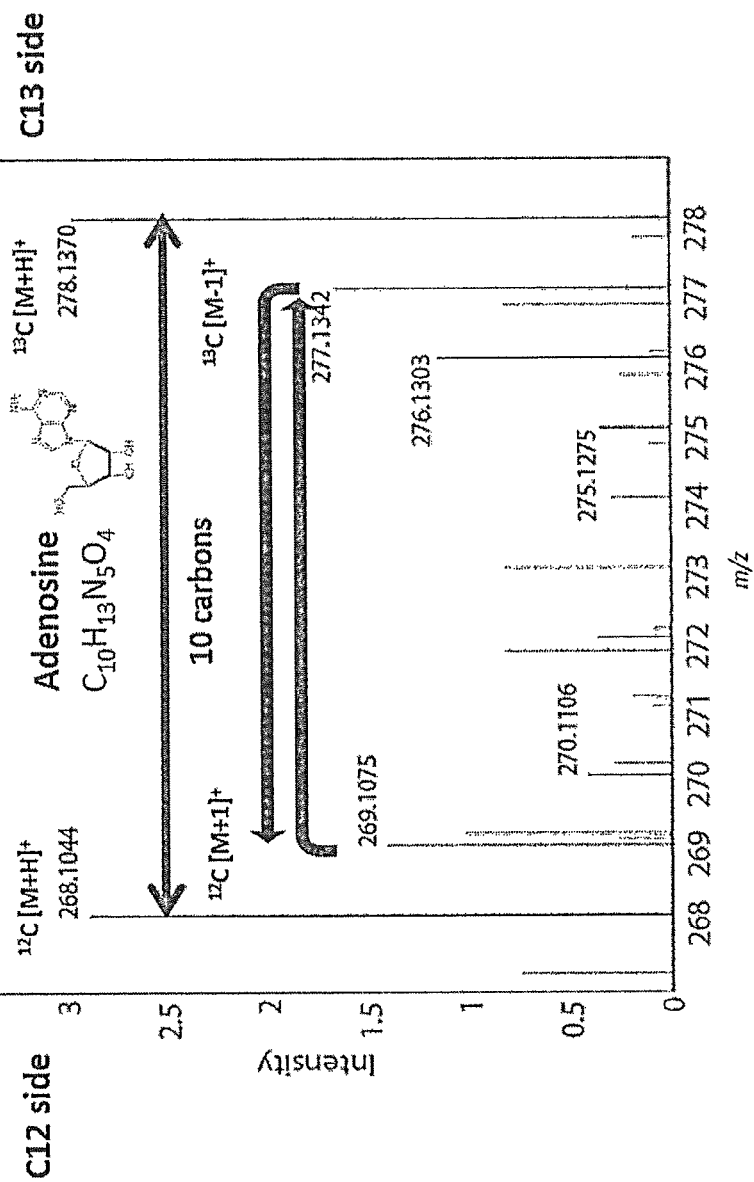
FIG. 11A shows mass spectral peaks present when adenosine is assayed using a sample containing equal amounts equal amounts of the compound containing 95% C12 and 5% C13 and the compound 95% C13 and 5% C12.
Figure 11B:
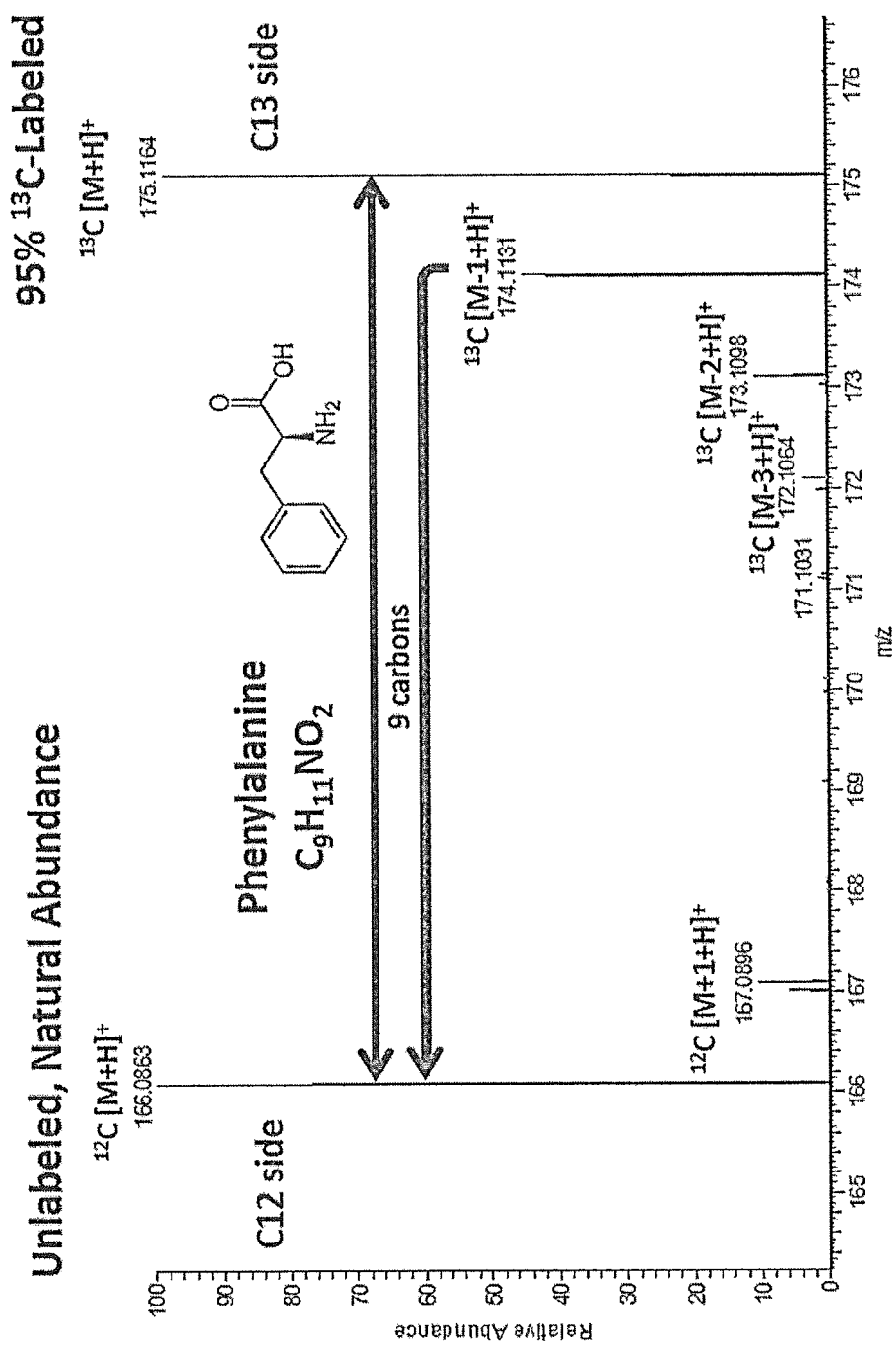
FIG. 11B shows mass spectral peaks present when phenylalanine is assayed using a sample containing equal amounts equal amounts of the compound containing 95% C12 and 5% C13 and the compound 95% C13 and 5% C12. It is noted that the number of carbon atoms present is provided by the difference in m/z values for the base peaks in each spectrum.

Because the IROA peaks are informatically self-contained, it is possible to correctly identify and quantify multiple co-eluting peaks. In the case of the Phenotypic Protocol, the IS can be created by a worker to provide support for the unique quantitation needs of the experimental system. Thus, a wheat researcher, can create a wheat C13-IS that can be used because it contains a chemical profile more reflective of wheat biochemistry, but this C13-IS is used primarily to find and identify IROA peaks in wheat and quantify their natural abundance counterparts. Although the triple redundancy of the Basic IROA protocol does not exist in the Phenotypic protocol, the signal is still redundant in that the 95% C13-IS provides a mass and number of carbons to determine exactly where the natural abundance monoisotopic signal is found (see FIGS. 5 and 6).

In the IROA workflow the same C13-IS is used in both the Matrix and the Clinical or experimental samples and the chemical information derived from the Matrix sample is used to verify and validate the compounds found in the clinical or experimental (Phenotypic) samples. The Phenotypic samples can be analyzed for chemical information to the same extent as the Matrix samples but this is not required. For instance, whereas the Matrix samples need to be analyzed to completely characterize every compound present in it, it can be sufficient to use the mass and retention information derived from the analysis of the Matrix to find the same compounds in the experimental or clinical samples, and use a higher acquisition rate than would be possible in the Matrix samples to achieve a higher quantitative accuracy.

The IROA Workflow

The IROA workflow combines and leverages the strengths of two previous IROA protocols, Basic IROA and Phenotypic IROA, and adds additional abilities to resolve chemical identity, normalize data, and enhance reproducibility between samples and across platforms whether similar or dissimilar.

IROA workflow makes the best use of the Basic IROA signal to catalog, validate, and characterize all of the compounds in the Matrix and thus C13-IS (which is common, and consistent to both the Basic and Phenotypic samples). By using the same C13-IS in the Phenotypic clinical or experimental samples, all the chemical identification and validation of the Matrix sample, a Basic IROA sample, can be applied to the experimental or clinical samples, which are Phenotypic samples.

In addition, the IROA Workflow applies an additional orthogonal identification second stage, such as Ion mobility, in-source or post source fragmentation, UV, IR, or the collection of other chemical characteristics, for each IROA peak in the Matrix, to provide additional unique physical attributes for every compound in the Matrix sample. If every compound in the Matrix is uniquely identified and is mappable to every clinical or experimental sample, this system supports completely reproducible compound identification irrespective of the analytical platform.

Therefore, the C13-IS in the experimental samples is capable of both providing a complete identification and quantitation solution without the need for a base-line chromatographic solution, and without the need for using the same orthogonal identification system on these samples. This is of import because the secondary systems can lower the temporal resolution and thereby lower the precision of the analytical measurement, but the measurement in Matrix is required for the mapping of chemical attributes and for identification purposes. The quantification of the Matrix is needed only at a lower level of precision.

On the other hand, for the clinical or experimental samples the quantification precision should be as high as possible. This overall solution has:
1) very high-level accuracy in identification and quantitation of compounds found in in the experimental sample due to the presence of the IS and mapped to the Corresponding compounds in Matrix,
2) a highly accurate and precise identification of all of the compounds in the Matrix samples, and
3) a rich and continuous quality assurance/quality control (QA/QC) for all instrumentation parameters (again derived from the Matrix sample) that is applied to the clinical or experimental sample, which is required for making human-relevant clinical biochemical measurements.

The chemical identification of the compounds in each Matrix injection derived from the secondary analytical streams, such as ion mobility, fragmentation, or other UV/vis, etc. provides sufficient characterization so that each compound can be uniquely identified based on these secondary features. Therefore, the combination of IROA pattern plus this secondary data, much of which is also IROA-based, provides a method to provide the reproducibility (quantitative and qualitative) needed to compare samples across wildly differing analytical platforms, or to adjust for day-to-day variances of instrumentation, and to assure both compound identity and quantification across differing platforms.

This workflow uses aspects of the Basic IROA protocol and a consistent Matrix sample to provide a (new) (QA/QC) that is independent of the instrument or the chromatographic systems.

When the benefits of each of these two protocols are combined into a single protocol they bring the strength of the triply-redundant Basic IROA protocol to build targeted libraries from highly standardized "Matrix" samples that are then used in the doubly redundant Phenotypic analysis of clinical samples.

The Matrix and clinical samples both contain the same concentration of the same 95% C13-IS. Because the Matrix samples additionally contain a matched C12-B that has the same chemical profile, their combined isotopic signals are symmetrical, mathematically balanced and unambiguously found. These libraries (catalogs of all compounds found) are created in Basic IROA samples at a higher level of stringency can be used, enabling a much broader assortment of compounds to be found even deep in mass spectral noise. Because the Phenotypic samples rely on the same 95% C13 internal standard, these libraries can be applied to coincidentally run samples with perfect matching expected and can be compared to non-coincidental samples through their common Matrix references.

The novelty of this approach derives from a previously mentioned attribute of the IROA peaks, namely that all of the isotopomers of a particular compound will share virtually identical chemical physical attributes except for mass, including UV, and to a limited extent the IR, as the additional neutrons have little influence on the electronic fields, charge distributions, or electron configurations. Thus, the IROA peaks will co-chromatograph and be seen as IROA peaks in the MS scans, and will also move through both ion mobility, SWATH fragmentations, as well as other processes, as complete units. The ability to find them beyond the MS level is a novel observation in this regard that permits the IROA workflow to use these IROA attributes to qualify and interpret IROA peaks at all stages of the analytical and identification process and make the IROA workflow possible.

Matrix and the C13-IS are always the same chemical mixture, at the same concentration, therefore these libraries provide a basis for a new cross-platform, cross-instrument, time independent QA/QC that makes it possible compare samples prepared in different laboratories, using different methods. The Matrix and C13-IS can be either biologically or chemically produced.

The Identification of Matrix Compounds

Each Matrix has a library associated with it when it is first prepared. The libraries are the compounds that can be seen reproducibly when a Matrix sample is chromatographically separated and the Basic IROA peaks in it are examined. Given the extreme diversity of possible chemical structures, the mass spectral data generated from chromatographic separation alone is not sufficient to identify most compounds, and is not even sufficient to identify a unique molecular formula for most molecules.

The Basic IROA peaks add to the monoisotopic mass the exact number of carbons in the molecule, and for most utilized libraries such as metabolite libraries this is sufficient to provide a unique molecular formula. However, for many molecular formulae, a given formula can be shared by a large number of compounds, hence, although IROA provides an assured formula it does not, in and of itself provide assured identification.

The IROA Workflow analyzes Matrix on a regular basis. In addition to the molecular formula for each IROA peak, if we can add collisional cross-section (CCS from IM), fragmentation data (ms/ms from SWATH or other techniques), UV, IR or any other physical characteristic of each compound in the Matrix and the library of compounds known to be contained in it, then the combination of assured molecular formula and these physical attributes become unique identifiers for each compound.

The IROA workflow analyzes the Matrix sample to determine the chromatographic behavior of all library compounds in the Matrix and IS on a daily basis. Because the concentration of the compounds in Matrix and IS, and their chromatographic behavior are identical, any identification made in Matrix can be mapped to IS. The key to the use of Matrix is that the clear IROA-formatted peaks maintain their integrity through msms where all fragments will show as IROA fragmentation, and similarly through IM where all the IROA peaks share a common CCS.

Illustrative Preparation of Matrix and IS

Whereas a Matrix (and IS) can be created to be a perfect match to any sample, most living things share a common core metabolism and therefore a "generic" matrix can be produced that is suitable for identifying and quantifying a wide variety of compounds in a wide variety of sample types. For instance, almost all living things use the same 20 amino acids and the same nucleotides, and share most of the same biochemical paths. Therefore, for good economic reasons one can opt to not create a specific Matrix (and IS) for a given sample type, but rather use a generic Matrix (and IS). A reasonable Matrix (and IS) can be created from single-celled or multi-celled organisms. Single-celled organisms such as fermentable yeasts, bacteria or alga where the efficiency of the fermentation process can be carefully controlled are preferred.

The preparation of a particularly preferred Matrix (and IS) is illustrated here, but a similar process could be followed to create a more specific Matrix:

1) A strain of S. cerevisiae that grows well on minimal media, such as S288C, or similar, is biochemically most competent, is selected and is tested to assure that it grows on a 95% 13C U-glucose as a main carbon source. If it passes this test and approximates normal growth habit to the eye of a fermentation expert it is deemed suitable;

2) The selected strain can be serially gown in sequentially larger containers until enough cells are available to initiate a large-scale fermentation, as for instance, a 20 Liter fermenter or larger. The media for these early fermentations is isotopically enriched glucose, with added minerals, including a nitrate or other nitrogen source, and vitamins. When sufficient cells are achieved, such as a 50 ml late-stage growth, this material is transferred into a 20 L fermenter in which the main carbon source for growth is isotopically labeled glucose, a nitrate or other nitrogen source, minerals and vitamins. The fermenter is aerobically sparged with carbon-dioxide free air for the duration of the fermentation to lower ethanol production and assure that the only $CO_2$ available is that produced from the isotopically labeled glucose. During the fermentation, additional isotopically labeled glucose is continuously added to replace that consumed. Throughout the course of the fermentation aliquots of fermentation fluids are removed for analysis, the cell density is determined, and media chemistry controlled. When the fermentation achieves an optimal density, late log-phase growth, but before it proceeds to senescence, the entire cell mass is harvested. The filtered cellular (yeast) mass is recovered from the media and frozen at −80° C.

3) The frozen yeast mass is removed from the freezer, resuspended in doubly distilled ion free water, and extruded through a French press, or other method of cellular disruption, at least three times; i.e., until it appears that substantially all of the yeast cells are ruptured. This ruptured lysate is permitted to autolyze; i.e, be digested by its own enzymes, for 24 hours at 45° C. to form a "yeast extract preparation".

4) The solid portions of the resulting yeast extract preparation are centrifugally separated as one fraction. The supernatant is filtered to remove fine particles, and then it is lyophilized as "yeast extract". The resulting yeast extract is a very rich biochemical mixture containing most of the stable biochemicals and their intermediates. Because this is meant to be a generic extract, the presence of unstable biochemical intermediates is minimized. If these relatively unstable biochemicals, such as ATP, etc., are sought then a specialized Matrix is needed.

For a Matrix, the above process is run to produce a 95% yeast extract (produced from yeast grown with 95% 13C U-glucose as a main carbon source) and, in a separate run, to produce a 5% yeast extract (produced from yeast grown with 5% 13C U-glucose as a main carbon source). The 95% yeast extract is used as the C13 half of the Matrix, and the Matrix is also the IS; i.e., these two compositions are obtained from exactly the same, homogeneous material in order to be chemically identical. (Note: they are both present in exactly the same concentration (20 mg per 40 ml) in both the Matrix and experimental samples. The 5% yeast extract (5% YE) is added in an equal proportion to the 95% yeast extract (95% YE) to provide the Matrix. Therefore, the Matrix, on mass spectral analysis, provides perfectly symmetrical sets of peaks. The Internal Standard is identical chemically and at its components are present at the same concentration as those in the Matrix, but the IS contains only 5% C12 material. The addition of the experimental sample provides the source of the C12 material which is to be measured.

The method for making up the Matrix and IS are as follows.

1) Weigh out an exact quantity of 95% YE, for instance, 90 mg. This is dissolved to create a 10 mg per ml solution by the addition of the appropriate amount of 50/50 water/ethanol, for this example exactly 9 ml of 95% YE is made.

2) Weigh out an exact quantity of 5% YE, for instance, 30 mg. This is dissolved to create a 10 mg per ml solution by the addition of the appropriate amount of 50/50 water/ethanol, for this example exactly 3 ml of 5% YE are made.

3) To make Matrix add equal volumes of the 95% YE solution, and the 5% YE solution. Thus, in this example add 3 ml of 95% YE to 3 ml of 5% YE, to form Matrix precursor.
   a) Aliquot 4 ml of the Matrix precursor into each injection vial, dry and seal under nitrogen and store at −80° C.

4) To make IS aliquot 50 µl of the 95% YE into a 2 ml vial, dry and seal under nitrogen, and store at −80° C.

In the case of Matrix, the dried Matrix injection vial contains 20 µl of 95% YE and 20 µl of 5% YE. When it is dissolved for injection, for instance by addition of 40 µl of dH2O, and mass spectrally analyzed, the resulting spectrum has very symmetrical, and very identifiable IROA peaks.

In the case of IS, the 2 ml vial contains 0.5 mg (or 0.500 mg) of the 95% YE. When this is dissolved in 1.2 ml (1200 µl) and 40 µl of this solution is added to a dried prepared experimental sample, each resulting experimental sample contains 20 mg of 95% YE, the same amount as is in the Matrix. The experimental samples will also contain the same compounds as the Matrix and IS, but they are present at natural abundance C13 levels, approximately 1.1%. Because mass spectral analysis of Matrix provided the identity of all of the Matrix compounds and thus those of the IS, the exact placement of the natural abundance peak is known for every compound. The height or area of the natural abundance compound is measured with complete knowledge of its identity and relative to the standard quantity of it 95% isotopomer.

Illustrated Case 1

Blood Work-Up in a Hospital/Clinical Lab

In the last 10 years mass spectrometry has moved forcefully into the field of clinical measurements because the flexibility, sensitivity, and cost are generally more favorable than traditional methods. However, in order to make a measurement, it is usually required to use an internal standard and to get a clean baseline separation between the compound(s) to be measured and other compounds that could affect the ionization efficiency, or cause confusion by accidently appearing where they are not expected, namely during the measurement period.

The reasons for this are simple. The internal standard is critical because the mass spectral ion source is potentially variable, the mass spectral signals are sensitive to tuning, ion suppression, solvent variability, or even atmospheric conditions. An internal standard that has a single peak, such as almost all non-IROA standards, can have its single peak confused with, or contaminated with an artefact that has a very similar mass.

When measuring natural abundance analytes this risk is normally mitigated by the dual approach of a) separating the analyte from all other compounds chromatographically and b) including an internal standard. As long as the internal standard co-chromatographs with the analyte and it is separated from potential confounders, the risk of a false measurement is considered low enough to accept the result. Although these steps can lower the risk to an acceptable level when a single compound is being measured, the risk is multiplied enormously when hundreds of compounds need to be measured simultaneously, and baseline separation cannot be assured.

A more secure system is thus needed:
- if an internal standard (IS) bore one or more unique identifying characteristics, that could assure it was the internal standard for a particular compound and it could not be mistaken for an artefact;
- if the IS co-chromatographed with the target compound, it would suffer all the source, and analytical variance of the target compound and would provide a perfect point of quantitative comparison; and
- if the IS co-chromatographed, shared all analytical variance, and could be uniquely matched to its target, a clean base-line separation would no longer be required to make a good analytical measurement.

The IROA C13-IS meets all of these criteria, 1) for each compound the shape of the IROA cluster is determined completely by its formula, 2) the compounds in the C13-IS co-chromatograph with their natural abundance (in the case of clinical or experimental samples) or their C12-B (in the case of matrix) isotopomers, and 3) are chemically otherwise identical.

Discovery Example 1

Illustratively, assume that the C13-1S and the Matrix are distributed as dried powder. The C13-IS is a dry powder in a 2 ml vial containing 500 µg C13-IS, and the Matrix is a dried powder in a glass injection vial with a glass insert that contains 20 µg C13-IS and 20 µg C12-B.

Further assume that there are 50 plasma samples to be analyzed, using a standard plasma preparation protocol such as:
- 50 µL of each of 50 samples of plasma are put into 50 1.8 ml Eppendorf tubes. These constitute the 50 samples to be analyzed;
- addition of 400 µL of cold precipitation solution (8:1:1 acetonitrile:methanol:acetone) with repeater pipette to make a solution of 1:8 (sample:solvent) ratio;
- vortex sample to ensure mixing, cool sample @ 4° C. for 30 minutes to further precipitate proteins; centrifuge at 20,000 rcf for 10 minutes at <10° C. to create a pellet of proteins; transfer 375 µL of supernatant to new, labeled tube making sure to leave behind protein pellet;
- dry the liquid sample using nitrogen, argon or other gas inert to reaction under the utilized conditions, in an Organomation Associates MultiVap® or similar apparatus, and store dried capped samples @−80° until ready to reconstitute.

Assume that the C13-1S and the Matrix are distributed as dried powder. The C13-IS is a dry powder in a 2 ml vial containing 500 µg C13-IS, and the Matrix is a dried powder in a glass injection vial with a glass insert that contains 20 µg C13-IS and 20 µg C12-B.

The C13-IS is reconstituted by addition of 1.25 ml cold 80% aqueous methanol; i.e., 20 µg per 50 µl, and vortexed to ensure mixing, then allowed to rest @ 4° C. for 10 minutes.

50 µl of the reconstituted C13-IS is used to reconstitute each dried capped sample. The sample is vortexed, allowed to rest 1 minute, and 40 µl is transferred to a glass injection vial with a glass insert.

The Matrix is reconstituted in 50 µl of 80% aqueous methanol, vortexed, and allowed to rest 1 minute.

The Matrix and 50 experimental samples are transferred to a mass spectrometer for chromatographic separation and MS analysis. All sample injections will be 4 µl injections, and thus contain the same concentration of C13-IS. The Matrix sample will be injected at least 5 times, randomly within the sequence of the experimental sample.

The data sets from these analyses are analyzed as follows:

Software such as the ClusterFinder™ software (IROA Technologies LLC, Ann Arbor, MI) can be used to find and characterize all of the IROA peaks that can be found across the multiple matrix injections. It accumulates all associated identifying characteristics for all IROA peaks found, including retention time (RT), C12 monoisotopic mass, C13 monoisotopic mass, number of carbons in the molecule, Ion mobility characteristics, fragmentation characteristics (in source, and post source), the amplitude of each peak in every IROA peak, the relationships between all IROA peaks, and any additional physical characteristics that were recorded.

The software uses all of the information found to identify each peak. Most peaks are well-known and previously well characterized, but possibly the software needs to create a new identifier. The molecular formula for each peak is derived from its IROA characteristics.

The software provides a file (typically written) that summarizes its finding with regard to each compound found. It can include RT (average and range, start of peak to end of peak), C12 monoisotopic mass (average and range), C13 monoisotopic mass (average and range), formula, and identity. On the standard high-resolution instruments available today, such as those made by Agilent, Thermo-Fisher, Sciex, and the like, the ranges found are quite tight.

This file is the basis of a targeted analysis of each experimental file, such that for every compound found in the Matrix sample, a detailed targeted analysis is run. Because the C13-IS is the same in every sample it is found in every sample. Because the mass of its natural abundance C13 monoisotopic is known it is possible to accurately quantify its presence.

If the C13-IS is seen but no natural abundance is seen, it can be labeled as absent.

If a C13-IS is absent but was seen in matrix, it can indicate a quality control issue.

The sum of all peaks within either the C13-IS and the natural abundance clusters is the numeric output.

Because the absolute amount of C13-IS in each vial is identical, the sum of all C13-IS peaks in each vial is fairly close if not identical. Deviations in this sum indicate problems either in the injection (if only one file shows it, or in the instrument if it shows a trend.

If normalization is needed, the assumption can be made that the sum of area on the natural abundance side is approximately equal, and if the C13-IS sums are relatively constant, then the natural abundance sum can be normalized to the C13-IS sum. (Note: This is only be needed in extreme cases.)

The outcome of this analysis is a standardized measure of all of the compounds present in the experimental (or clinical) sample. For each sample there is an associated quality measure. The standardization to a consistent Matrix sample assures nomenclature, within the sample set, across days within similar instruments, or even across widely divergent instruments, although the performance differences across different instruments will likely cause some consistent differences that can be well characterized due to the instruments source, lensing, detectors, etc. Nonetheless, it is expected that the majority of compounds will be mappable across widely differing platforms.

Illustrated Case 2
Urine Work-Up in a Hospital/Clinical Lab

Although there are some similarities, the chemistry of urine is very different from that of plasma so urine is used to illustrate a variation of the IROA Workflow one in which the Matrix is custom-made for urine.

Consider the following as one possible variation:

500 (or more) liters of urine are acquired and dried. The powdered natural abundance urine is then split into two aliquots one that represents 90% of the total amount obtained (aliquot A), and the other that represents 10% of that total amount (aliquot B). Each aliquot is derivatized using an IROA-based derivatization reagent, such as phenylisothiocyanate (PITC), although many others could be used. There are seven carbons in the resulting phenylthiocarbamyl reaction product, so if derivatization is done using both a 5% $^{13}$C PITC and a 95% $^{13}$C PITC, the resulting products can be mixed together to yield seven carbon IROA peak patterns.

In a similar manner, 5% $^{13}$C phenylhydrazine and a 95% $^{13}$C phenylhydrazine that each contain six carbon atoms can be used to derivatize aldehydes and ketones in a sample such as urine as discussed above for PITC. In the presence of excess phenylhydrazine, some sugars add two phenylhydrazine groups to form a diphenylosazone. Phenylsemicarbazide that contains seven carbon atoms can similarly be used to react with ketones and aldehydes present in a sample to be analyzed.

The above-discussed reagents react with and bond to primary amines and aldehydes/ketones, respectively. A worker of ordinary skill can readily consult common texts such as Green et al., *Protective Groups in Organic Synthesis*, 3$^{rd}$ ed., John Wiley & Sons, Inc. New York, 1999, or Lundblad, *Techniques in Protein Modification*, CRC Press, Boca Raton, 1995, to identify further reagents that can be used to convert other functional groups such as hydroxyl groups, thiols and carboxylic acids present in compounds of an all natural abundance sample into an 7 IROA sample as discussed herein.

Therefore, with a view to the amounts needed reacting aliquot A with 95% $^{13}$C PITC and aliquot B with 5% $^{13}$C PITC yields two mixed products in which all amine-containing compounds in urine are converted to their phenylthiocarbamyl equivalents. The material from aliquot A and aliquot B are mixed in equal quantities to form a Urine-specific Matrix, whereas the additional material from aliquot A provides a comparable C13-IS when added to the experimental samples.

Once these reagents are at hand a protocol similar to that of Illustrated case 1 can be followed to quantitate all of the amine-containing compounds in urine, where they are plentiful. Different derivatization reagents can be used to highlight other chemical functionalities. In fact, if the products are as stable and relatively non-reactive to one another, two or more can be individually created and then pooled to create a more complex Matrix.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed is:

1. A method of quality assurance and/or quality control on the operational constancy of a mass spectral apparatus and associated ion mobility channel and chromatographic apparatus, when present, that comprises the steps of:
   a) carrying out one or more mass spectral analyses of experimental samples;
   b) carrying out a mass spectral analysis on multiple isotopic ratio outlier analysis (IROA) standard samples each of which is an aliquoted composition of biologically-produced metabolite compounds, each of said metabolite compounds having a molecular weight of about 2000 AMU or less, and each of said metabolite compounds being present as paired first and second isotopically-labeled compounds that are equally present at two predetermined balances for a non-hydrogen/deuterium atom present in said compounds, said first isotopically-labeled compounds containing about 2 to about 10% of a first isotope and about 90 to about 98% of a second isotope of said non-hydrogen/deuterium atom, and said second isotopically-labeled compounds containing about 90 to about 98% of said first isotope and about 2 to about 10% of said second isotope of the same non-hydrogen/deuterium atom, said first and second isotopes being stable to radioactive decay and other than hydrogen and deuterium, wherein mass spectral analysis of each IROA standard sample provides symmetrical patterns of peaks of said paired first and second isotopically-labeled compounds present that reflect i) the identity and number of peak pairs found, ii) their chromatographic retention time, iii) the amplitude of each peak pair and the sum of all peak pairs, iv) the resolution and sensitivity of the mass spectral analysis and v) allows the elimination of artifacts and noise during the course of carrying out analyses of both the standard and experimental samples, c) storing the values determined from the standard sample analyses to determine trends in instrumentation, and d) evaluating the mass spectral analyses of step b) to determine the existence of differing results, and if found, using those differing results to correct for variances in measured aspects in the results of the experimental samples.

2. The method according to claim 1, wherein said biologically-produced metabolite compounds are obtained from a cell lysate preparation obtained from culture of single-celled or multi-celled organisms, and the metabolite compounds are universally labeled.

3. The method according to claim 2, wherein said cell lysate preparation is obtained from culture of single-celled organisms and the metabolite compounds are universally labeled.

4. The method according to claim 1, wherein said first and second isotopes of the same atom are one or more elements selected from the group consisting of isotopes of carbon ($^{12}C$ and $^{13}C$), nitrogen ($^{14}N$ and $^{15}N$), oxygen ($^{16}O$, $^{17}O$, or $^{18}O$), sulfur ($^{32}S$, $^{33}S$, $^{34}S$, or $^{36}S$), chlorine ($^{35}Cl$ and $^{37}Cl$), magnesium ($^{24}Mg$, $^{25}Mg$ and $^{26}Mg$), silicon ($^{27}Si$, $^{28}Si$ and $^{29}Si$), calcium ($^{40}Ca$, $^{42}Ca$, $^{43}Ca$, and $^{44}Ca$), and bromine ($^{19}Br$ and $^{81}Br$).

5. The method according to claim 1, wherein said first and second isotopes of the same atom are $^{12}C$ and $^{13}C$.

6. The method according to claim 1, wherein each of said metabolite compounds has a molecular weight of about 1500 AMU or less.

* * * * *